US008568993B2

(12) United States Patent (10) Patent No.: US 8,568,993 B2
Regnier et al. (45) Date of Patent: Oct. 29, 2013

(54) DETECTION OF GLYCOPEPTIDES AND GLYCOPROTEINS FOR MEDICAL DIAGNOSTICS

(75) Inventors: Fred E. Regnier, West Lafayette, IN (US); Stephen B. Hooser, West Lafayette, IN (US); Christina R. Wilson, Lafayette, IN (US); Wonryeon Cho, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 779 days.

(21) Appl. No.: 12/164,676

(22) Filed: Jun. 30, 2008

(65) Prior Publication Data

US 2009/0053828 A1 Feb. 26, 2009

Related U.S. Application Data

(60) Provisional application No. 60/958,016, filed on Jul. 2, 2007.

(51) Int. Cl.
*G01N 31/00* (2006.01)
*G01N 33/53* (2006.01)

(52) U.S. Cl.
USPC ............ 435/7.21; 435/4; 435/7.1; 435/287.9; 436/501; 436/518; 436/525; 436/529; 436/535; 436/809; 427/287; 427/337; 427/338; 530/300; 530/350

(58) Field of Classification Search
None
See application file for complete search history.

(56) References Cited

U.S. PATENT DOCUMENTS 6,864,099 B2 3/2005 Regnier
6,872,575 B2 3/2005 Regnier

FOREIGN PATENT DOCUMENTS

WO WO2009/006382 A1 1/2009

OTHER PUBLICATIONS

Rabina et al., Analytical Biochemistry, vol. 246, pp. 71-78, 1997.*
Mas et al., Glycobiology, 1998, pp. 605-613, vol. 8, No. 6, 1998.*
Qiu and Regnier (Analytical Chemistry, 2005, vol. 77, pp. 7225-7231).*
International Search Report From International Patent Application No. PCT/US2008/068742 dated Nov. 27, 2008.
Agarwal, S.; Ferreira, V.P.; Cortes, C.; Pangburn, M.K.; Rice, P.A.; Ram, S. "An Evaluation of the Role of Properdin in Alternative Pathway Activation on *Neisseria meningitidis* and *Neisseria gonorrhoeae*," *J. Immunol.*, 2010, 185, 507-516.
An, H.J.; Miyamoto, S.; Lancaster, K.S.; Kirmiz, C.; Li, B.; Lam, K.S.; Leiserowitz, G.S.; Lebrilla, C.B. "Profiling of Glycans in Serum for the Discovery of Potential Biomarkers for Ovarian Cancer," *J. Proteome Res.*, 2006, 5, 1626-1635.
Anderson, L.; Hunter, C.L. "Quantitative Mass Spectrometric Multiple Reaction Monitoring Assays for Major Plasma Proteins," *Mol. Cell. Proteomics*, 2006, 5, 573-588.
Apweiler, R.; Hermjakob, H.; Sharon, N. "On the Frequency of Protein Glycosylation, as Deduced From Analysis of the Swiss-Prot Database," *Biochim. Biophys. Acta*, 1999, 1473, 4-8.
Asara, J.M.; Zhang, X.; Zheng, B.; Maroney, L.A.; Christofk, H.R.; Wu, N.; Cantley, L.C. "In-Gel Stable Isotope Labeling for Relative Quantification Using Mass Spectrometry," *Nature Protocols*, 2006, 1, 46-51.
Baba, S.; Takahashi, T.; Kasama, T.; Fujie, M.; Shirasawa, H. "A Novel Polymorphism of Human Serum Amyloid a Protein, SAA1 Gamma, is Characterized by Alanines at Both Residues 52 and 57," *Arch. Biochem. Biophys.*, 1993, 303, 361-366.
Baba, S.; Takahashi, T.; Kasama, T.; Shirasawa, H. "Identification of Two Novel Amyloid a Protein Subsets Coexisting in an Individual Patient of Aa-Amyloidosis," *Biochim. Biophys. Acta*, 1992, 1180, 195-200.
Bailey, S.D.; Xie, C.; Do, R.; Montpetit, A.; Diaz, R.; Mohan, V.; Keavney, B.; Yusuf, S.; Gerstein, H.C.; Engert, J.C.; Anand, S. "Variation at the NFATC2 Locus Increases the Risk of Thiazolidinedione-Induced Edema in the Diabetes REduction Assessment with Ramipril and Rosiglitazone Medication (DREAM) Study," *Diabetes Care*, 2010, 33, 2250-2253.
Beach, C.M.; De Beer, M.C.; Sipe, J.D.; Loose, L.D.; De Beer, F.C. "Human Serum Amyloid A Protein. Complete Amino Acid Sequence of a New Variant," *Biochem. J.*, 1992, 282, 615-620.
Becker, D.J.; Lowe, J.B. "Review—Fucose: Biosynthesis and Biological Function in Mammals," *Glycobiology*, 2003, 13, 41R-53R.
Benditt, E.P.; Eriksen, N.; Hermodson, M.A.; Ericsson, L.H. "The Major Proteins of Human and Monkey Amyloid Substance: Common Properties Including Unusual N-Terminal Amino Acid Sequences," *FEBS Lett.*, 1971, 19, 169-173.
Betts, J.C.; Edbrooke, M.R.; Thakker, R.V.; Woo, P. "The Human Acute-Phase Serum Amyloid a Gene Family: Structure, Evolution and Expression in Hepatoma Cells," *Scand. J. Immunol.*, 1991, 34, 471-482.
Borgotio, C.A.; Grass, L.; Soosaipillai, A.; Yousef, G.M.; Petraki, C.D.; Howarth, D.H.C.; Fracchioli, S.; Katsaros, D.; Diamandis, E.P. "Human Kallikrein 14: A New Potential Biomarker for Ovarian and Breast Cancer," *Cancer Res.* 2003, 63, 9032-9041.
Brockhausen, I. "Mucin-Type *O*-Glycans in Human Colon and Breast Cancer: Glycodynamics and Functions," *EMBO*, 2006, 7, 599-604.
Chakraborty, A.; Regnier, F.E. "Global Internal Standard Technology for Comparative Proteomics," *J. Chromatography A*, 2002, 949, 173-184.
Cho, W.; Jung, K.; Regnier, F.E. "Use of Glycan Targeting Antibodies to Identify Cancer-Associated Glycoproteins in Plasma of Breast Cancer Patients," *Anal. Chem.*, 2008, 80, 5286-5292.
Coleman, M.P.; Murray, J.C.; Willard, H.F.; Nolan, K.F.; Reid, K.B.M.; Blake, D.J.; Lindsay, S.; Bhattacharya, S.S.; Wright, A.; Davies, K.E. "Genetic and Physical Mapping Around the Properdin P Gene," *Genomics*, 1991, 11, 991-996.

(Continued)

*Primary Examiner* — Lisa Cook
(74) *Attorney, Agent, or Firm* — Brinks Hofer Gilson & Lione

(57) ABSTRACT

A diagnostic method for determining the absence or presence of a disease is provided. The method includes assaying the amount and/or types of glycopeptides in a sample from a subject, and comparing these to the amount and types of reference glycopeptides. The method may include the use of a stable isotope label, affinity selection, immunoaffinity chromatography, and glycoproteomics techniques, to identify and quantify changes in glycosylated peptides or glycosylated proteins associated with cancers such as malignant lymphoma or breast cancer, to monitor patient's response to therapy, and to monitor disease recurrence.

25 Claims, 8 Drawing Sheets

(56) References Cited

OTHER PUBLICATIONS

Danik, M.; Chabot, J-G.; Mercier, C.; Benabid, A-L.; Chauvin, C.; Quirion, R.; Suh, M. "Human Gliomas and Epileptic Foci Express High Levels of a mRNA Related to Rat Testicular Sulfated Glycoprotein 2, a Purported Marker of Cell Death," *Proc. Natl. Acad. Sci. U.S.A.*, 1991, 88, 8577-8581.

Deuel, T.F.; Keim, P.S.; Farmer, M.; Heinrikson, R.L. "Amino Acid Sequence of Human Platelet Factor 4," *Proc. Natl. Acad. Sci. U.S.A.*, 1977, 74, 2256-2258.

Drake, R.R.; Schwegler, E.E.; Malik, G.; Diaz, J.; Black, T.; Mehta, A.; Semmes, O.J. "Lectin Capture Strategies Combined With Mass Spectrometry for the Discovery of Serum Glycoprotein Biomarkers," *Mol. Cell. Proteomics*, 2006, 5, 1957-1967.

Dubrac, A.; Quemener, C.; Lacazette, E.; Lopez, F.; Zanibellato, C.; Wu, W-G.; Bikfalvi, A.; Prats, H. "Functional Divergence Between 2 Chemokines is Conferred by Single Amino Acid Change," *Blood*, 2010, 116, 4703-4711.

Ducret, A.; Bruun, C.F.; Bures, E.J.; Marhaug, G.; Husby, G.; Aebersold, R. "Characterization of Human Serum Amyloid A Protein Isoforms Separated by Two-Dimensional Electrophoresis by Liquid Chromatography/Electrospray Ionization Tandem Mass Spectrometry," *Electrophoresis*, 1996, 17, 866-876.

Edwards, D.P.; Grzyb, K.T.; Dressler, L.G.; Mansel, R.E.; Zava, D.T.; Sledge, Jr., G.W.; McGuire, W.L. "Monoclonal Antibody Identification and Characterization of a $M_r$ 43,000 Membrane Glycoprotein Associated With Human Breast Cancer," *Cancer Res.*, 1986, 46, 1306-1317.

Ein, D.; Kimura, S.; Terry, W.D.; Magnotta, J.; Glenner, G.G. "Amino Acid Sequence of an Amyloid Fibril Protein of Unknown Origin," *J. Biol. Chem.*, 1972, 247, 5653-5655.

Fearon, D.T. "Activation of the Alternative Complement Pathway," *CRC Crit. Rev. Immunol.*, 1979, 1, 1-32.

GenBank Accession # AAA 60321 (Jan. 9, 1995).

GenBank Accession # AAK 31373 (Jun. 1, 2001).

GenBank Accession # AAI 07767 (Jul. 21, 2006).

GenBank Accession # AAH 73767 (Jan. 9, 1995 revised Jul. 28, 2005).

GenBank Accession # AAB 59550 (Oct. 16, 2002).

GenBank Accession # NP 002610 (Mar. 24, 1999 revised Feb. 6, 2011).

GenBank Accession # NP 002612 (Mar. 24, 1999 revised Feb. 13, 2011).

GenBank Accession # P 02735 (Apr. 24, 1993 revised Feb. 8, 2011).

GenBank Accession # AAH 05046 (Jul. 15, 2006).

Gerhard, D.S.; Wagner, L.; Feingold, E.A.; Shenmen, C.M.; Grouse, L.H.; Schuler, G.; Klein, S.L.; Old, S.; Rasooly, R.; Good, P.; Guyer, M.; Peck, A.M.; Derge, J.G.; Lipman, D.; Collins, F.S.; Jang, W.; Sherry, S.; Feolo, M.; Misquitta, L.; Lee, E.; Rotmistrovsky, K.; Greenhut, S.F.; Schaefer, C.F.; Buetow, K.; Bonner, T.I.; Haussler, D.; Kent, J.; Diekhaus, M.; Furey, T.; Brent, M.; Prange, C.; Schreiber, K.; Shapiro, N.; Bhat, N.K.; Hopkins, R.F.; Hsie, F.; Driscoll, T.; Soares, M.B.; Bonaldo, M.F.; Casavant, T.L.; Scheetz, T.E.; Brownstein, M.J.; Usdin, T.B.; Toshiyuki, S.; Carninci, P.; Piao, Y.; Dudekula, D.B.; Ko, M.S.H.; Kawakami, K.; Suzuki, Y.; Sugano, S.; Gruber, C.E.; Smith, M.R.; Simmons, B.; Moore, T.; Waterman, R.; Johnson, S.L.; Ruan, Y.; Wei, C.L.; Mathavan, S.; Gunaratne, P.H.; Wu, J.; Garcia, A.M.; Hulyk, S.W.; Fuh, E.; Yuan, Y.; Sneed, A.; Kowis, C.; Hodgson, A.; Muzny, D.M.; McPherson, J.; Gibbs, R.A.; Fahey, J.; Helton, E.; Ketteman, M.; Madan, A.; Rodrigues, S.; Sanchez, A.; Whiting, M.; Madan, A.; Young, A.C.; Wetherby, K.D.; Granite, S.J.; Kwong, P.N.; Brinkley, C.P.; Pearson, R.L.; Bouffard, G.G.; Blakesly, R.W.; Green, E.D.; Dickson, M.C.; Rodriguez, A.C.; Grimwood, J.; Schmutz, J.; Myers, R.M.; Butterfield, Y.S.N.; Griffith, M.; Griffith, O.L.; Krzywinski, M.I.; Liao, N.; Morrin, R.; Palmquist, D.; Petrescu, A.S.; Skalska, U.; Smailus, D.E.; Stott, J.M.; Schnerch, A.; Schein, J.E.; Jones, S.J.M.; Holt, R.A.; Baross, A.; Marra, M.A.; Clifton, S.; Makowski, K.A.; Bosak, S.; Malek, J. "The Status, Quality, and Expansion of the NIH Full-Length cDNA Project: The Mammalian Gene Collection (MGC)," *Genome Res.*, 2004, 14, 2121-2127.

Goundis, D.; Holt, S.M.; Boyd, Y.; Reid, K.B.M. "Localization of the Properdin Structural Locus to Xp11.23-Xp21.1," *Genomics*, 1989, 5, 56-60.

Hartmann, S.; Hofsteenge, J. "Properdin, the Positive Regulator of Complement, is Highly *C*-Mannosylated," *J. Biol. Chem.*, 2000, 275, 28569-28574.

Hermodson, M.; Schmer, G.; Kurachi, K. "Isolation, Crystallization, and Primary Amino Acid Sequence of Human Platelet Factor 4," *J. Biol. Chem.*, 1977, 252, 6276-6279.

Howard, B.A.; Wang, M.Z.; Campa, M.J.; Corro, C.; Fitzgerald, M.C.; Patz, Jr., E.F. "Identification and Validation of a Potential Lung Cancer Serum Biomarker Detected by Matrix-Assisted Laser Desorption/Ionization-Time of Flight Spectra Analysis," *Proteomics*, 2003, 3, 1720-1724.

Janis, L.J.; Regnier, F.E. "Dual-Column Immunoassays Using Protein G Affinity Chromatography," *Anal. Chem.*, 1989, 61, 1901-1906.

Ji, J.; Chakraborty, A.; Geng, M.; Zhang, X.; Amini, A.; Bina, M.; Regnier, F. "Strategy for Qualitative and Quantitative Analysis in Proteomics Based on Signature Peptides," *J. Chromatography B*, 2000, 745, 197-210.

Julka, S.; Regnier, F.E. "Recent Advancements in Differential Proteomics Based on Stable Isotope Coding," *Briefings in Functional Genomics and Proteomics*, 2005, 4, 158-177.

Khilanani, P; Chou, T-H.; Ratanatharathorn, V.; Kessel, D. "Evaluation of Two Plasma Fucosyltransferases as Marker Enzymes in Non-Hodgkin's Lymphoma," *Cancer*, 1978, 41, 701-705.

Kiernan, U.A.; Tubbs, K.A.; Nedelkov, D.; Niederkofler, E.E.; Nelson, R.W. "Detection of Novel Truncated Forms of Human Serum Amyloid A Protein in Human Plasma," *FEBS Lett.*, 2003, 537, 166-170.

Kitamura, N.; Kitagawa, H.; Fukushima, D.; Takagaki, Y.; Miyata, T.; Nakanishi, S. "Structural Organization of the Human Kininogen Gene and a Model for Its Evolution," *J. Biol. Chem.*, 1985, 260, 8610-8617.

Kluve-Beckerman, B.; Dwulet, F.E.; Bensen, M.D. "Human Serum Amyloid A. Three Hepatic mRNAs and the Corresponding Proteins in One Person," *J. Clin. Invest.*, 1988, 82, 1670-1675.

Kluve-Beckerman, B.; Long, G.L.; Benson, M.D. "DNA Sequence Evidence for Polymorphic Forms of Human Serum Amyloid A (SAA)," *Biochem. Genet.*, 1986, 24, 795-803.

Legnani, C.; Cini, M.; Pili, C.; Boggian, O.; Frascaro, M.; Palareti, G. "Evaluation of a New Automated Panel of Assays for the Detection of Anti-PF4/Heparin Antibodies in Patients Suspected of Having Heparin-Induced Thrombocytopenia," *Thromb. Haemost.*, 2010, 104, 402-409.

Levin, M.; Franklin, E.C.; Frangione, B.; Pras, M. "The Amino Acid Sequence of a Major Nonimmunoglobulin Component of Some Amyloid Fibrils," *J. Clin. Invest.*, 1972, 51, 2773-2776.

Linkov, F.; Stack, B.; Yurkovetsky, Z.; Poveda, S.; Lokshin, A.; Ferris, R.L. "Head and Neck Squamous and Thyroid Carcinomas: Multiplexed Luminex Approaches for Early Detection," *Expert Opin. Med. Diagn.*, 2007, 1, 129-136.

Lucas, S.R.R.; Coelho, B.M.P.; Marquezi, M.L.; Franchini, M.L.; Miyashiro, S.I.; de Benedetto Pozzi, D.H. "Carmustine, Vincristine, and Prednisone in the Treatment of Canine Lymphosarcoma," *J. Amer. Anim. Hosp. Assoc.*, 2004, 40, 292-299.

Maione, T.E.; Gray, G.S.; Petro, J.; Hunt, A.J.; Donner, a.L.; Bauer, S.I.; Carson, H.F.; Sharpe, R.J. "Inhibition of Angiogenesis by Recombinant Human Platelet Factor-4 and Related Peptides," *Science*, 1990, 247, 77-79.

Matta, A.; DeSouza, L.V.; Shukla, N.K.; Gupta, S.D.; Ralhan, R.; Siu, K.W.M. "Prognostic Significance of Head-and-Neck Cancer Biomarkers Previously Discovered and Identified Using iTRAQ-Labeling and Multidimensional Liquid Chromatography—Tandem Mass Spectrometry," *J. Proteome Res.*, 2008, 7, 2078-2087.

Mayes, K.K.; Weiler, J.M. "Detection of Properdin mRNA in Human Peripheral Blood Monocytes and Spleen," *J. Lab. Clin. Med.*, 1992, 120, 762-766.

McDonald, W.H.; Yates, III, J.R. "Shotgun Proteomics and Biomarker Discovery," *Disease Markers*, 2002, 18, 99-105.

Monzavi-Karbassi, B.; Whitehead, T.L..; Jousheghany, F.; Artaud, C.; Hennings, L.; Shaaf, S.; Slaughter, A.; Korourian, S.; Kelly, T.; Blaszczyk-Thurin, M.; Kieber-Emmons, T. "Deficiency in Surface

(56) References Cited

OTHER PUBLICATIONS

Expression of E-Selectin Ligand Promotes Lung Colonization in a Mouse Model of Breast Cancer," *Int. J. Cancer*, 2005, 117, 398-408.

Mosnier, L.O. "Platelet Factor 4 Inhibits Thrombomodulin-Dependent Activation of Thrombin-Activatable Fibrinolysis Inhibitor (TAFI) by Thrombin," *J. Biolog. Chem.*, 2011, 286, 502-510.

Møyner, K.; Sletten, K.; Husby, G.; Natvig, J.B. "An Unusually Large (83 Amino Acid Residues) Amyloid Fibril Protein AA From a Patient With Waldenstrom's Macroglobulinaemia and Amyloidosis," *Scand. J. Immunol.*, 1980, 11, 549-554.

Nath, N.; Lowery, C.T.; Niewiarowski, S. "Antigenic and Antiheparin Properties of Human Platelet Factor 4 (PF4)," *Blood*, 1975, 45, 537-550.

Nolan, K.F.; Kaluz, S.; Higgins, J.M.G.; Goundis, D.; Reid, K.B.M. "Characterization of the Human Properdin Gene," *Biochem. J.*, 1992, 287, 291-297.

Nolan, K.F.; Schwaeble, W.; Kaluz, S.; Dierich, M.P.; Reid, K.B.M. "Molecular Cloning of the cDNA Coding for Properdin, a Positive Regulator of the Alternative Pathway of Human Complement," *Eur. J. Immunol.*, 1991, 21, 771-776.

Oda, Y.; Senaha, T.; Matsuno, Y.; Nakajima, K.; Naka, R.; Kinoshita, M.; Honda, E.; Furuta, I.; Kakehi, K. "A New Fungal Lectin Recognizing α(1-6)-Linked Fucose in the *N*-Glycan," *J. Biol. Chem.*, 2003, 278, 32439-32447.

Orntoft, T.F.; Vestergaard, E.M. "Clinical Aspects of Altered Glycosylation of Glycoproteins in Cancer," *Electrophoresis*, 1999, 20, 362-371.

Parmelee, D.C.; Titani, K.; Ericsson, L.H.; Eriksen, N.; Benditt, E.P.; Walsh, K.A. "Amino Acid Sequence of Amyloid-Related Apoprotein (apoSAA$_1$) From Human High-Density Lipoprotein," *Biochemistry*, 1982, 21, 3298-3303.

Prelli, F.; Pras, M.; Frangione, B. "Degradation and Deposition of Amyloid AA Fibrils are Tissue Specific," *Biochemistry*, 1987, 26, 8251-8256.

Qiu, R.; Regnier, F.E. "Comparative Glycoproteomics of N-Linked Complex-Type Glycoforms Containing Sialic Acid in Human Serum," *Anal. Chem.*, 2005, 77, 7225-7231.

Rabina, J.; Smithers, N.; Britten, C.J.; Renkonen, R. "A Time-Resolved lmmunofluorometric Method for the Measurement of Sialyl Lewis x-Synthesizing α 1,3-Fucosyltransferase Activity," *Anal. Biochem.*, 1997, 246, 71-78.

Regnier, F.E.; Julka, S. "Primary Amine Coding as a Path to Comparative Proteomics," *Proteomics*, 2006, 6, 3968-3979.

Rosenfeld, R.; Bangio, H.; Gerwig, G.J.; Rosenberg, R.; Aloni, R.; Cohen, Y.; Amor, Y.; Plaschkes, I.; Kamerling, J.P.; Maya, R.B-Y. "A Lectin Array-Based Methodology for the Analysis of Protein Glycosylation," *J. Biochem. Biophys. Methods*, 2007, 70, 415-426.

Ross, P.L.; Huang, Y.N.; Marchese, J.N.; Williamson, B.; Parker, K.; Hattan, S.; Khainovski, N.; Pillai, S.; Dey, S.; Daniels, S.; Purkoyastha, S.; Juhasz, P.; Martin, S.; Bartlet-Jones, M.; He, F.; Jacobson, A.; Pappin, D.J. "Multiplexed Protein Quantitation in Saccharomyces cerevisiae Using Amine-reactive Isobaric Tagging Reagents," *Mol. Cell. Proteomics*, 2004, 3, 1154-1169.

Rossowski, W.; Srivastava, B.I.S. "Glycosyltransferase Activities in Leukemic Cells from Patients and Human Leukemic Cell Lines," *Eur. J. Cancer and Clin. Oncol.*, 1983, 19, 1431-1437.

Rupar, C.A.; Cook, G.M.W. "Glycoprotein Biosynthesis in Quiescent and Stimulated Thymocytes and a T-Cell Lymphoma," *Biochem. J.*, 1982, 201, 377-385.

Seitsonen, S.; Onkamo, P.; Torniainen, S.; Ihalainen, M.; Immonen, I.; Meri, N.; Jarvela, I. "Screening of DNA-Variants in the Properdin Gene (CFP) in Age-Related Macular Degeneration (AMD)," *Mol. Immunol.*, 2010, 47, 1334-1336.

Siezenga, M.A.; van der Geest, R.N.; Mallat, M.J.K.; Rabelink, T.J.; Daha, M.R.; Berger, S.P. "Urinary Properdin Excretion is Associated With Intrarenal Complement Activation and Poor Renal Function," *Nephrol Dial Transplant*, 2010, 25, 1157-1161.

Sipe, J.D.; Colten, H.R.; Goldberger, G.; Edge, M.D.; Tack, B.F.; Cohen, A.S.; Whitehead, A.S. "Human Serum Amyloid A (SAA): Biosynthesis and Postsynthetic Processing of PreSAA and Structural Variants Defined by Complementary DNA," *Biochemistry*, 1985, 24, 2931-2936.

Sletten, K.; Husby, G. "The Complete Amino-Acid Sequence of Non-Immunoglobulin Amyloid Fibril Protein AS in Rheumatoid Arthritis," *Eur. J. Biochem.*, 1974, 41, 117-125.

K.; Sletten, K.; Husby, G.; Natvig, J.B. "The Complete Amino Acid Sequence of an Amyloid Fibril Protein AA$^1$ of Unusual Size (64 Residues)," *Biochem. Biophys. Res. Commun.*, 1976, 69, 1925.

Steinkasserer, A.; Weiss, E.H.; Schwaeble, W.; Linke, R.P. "Heterogeneity of Human Serum Amyloid A Protein. Five Different Variants From One Individual Demonstrated by cDNA Sequence Analysis," *Biochem. J.*, 1990, 268, 187-193.

Strausberg, R.L.; Feingold, E.A.; Grouse, L.H.; Derge, J.G.; Klausner, R.D.; Collins, F.S.; Wagner, L.; Shenmen, C.M.; Schuler, G.D.; Altschul, S.F.; Zeeberg, B.; Buetow, K.H.; Schaefer, C.F.; Bhat, N.K.; Hopkins, R.F.; Jordan, H.; Moore, T.; Max, S.I.; Wang, J.; Hsieh, F.; Diatchenko, L.; Marusina, K.; Farmer, A.A.; Rubin, G.M.; Hong, L.; Stapleton, M.; Soares, M.B.; Bonaldo, M.F.; Casavant, T.L.; Scheetz, T.E.; Brownstein, M.J.; Usdin, T.B.; Toshiyuki, S.; Carninci, P.; Prange, C.; Raha, S.S.; Loquellano, N.A.; Peters, G.J.; Abramson, R.D.; Mullahy, S.J.; Bosak, S.A.; McEwan, P.J.; McKernan, K.J.; Malek, J.A.; Gunaratne, P.H.; Richards, S.; Worley, K.C.; Hale, S.; Garcia, A.M.; Gay, L.J.; Hulyk, S.W.; Villalon, D.K.; Muzny, D.M.; Sodergren, E.J.; Lu, X.; Gibbs, R.A.; Fahey, J.; Helton, E.; Ketteman, M.; Madan, A.; Rodrigues, S.; Sanchez, A.; Whiting, M.; Madan, A.; Young, A.C.; Shevchenko, Y.; Bouffard, G.G.; Blakesley, R.W.; Touchman, J.W.; Green, E.D.; Dickson, M.C.; Rodriguez, A.C.; Grimwood, J.; Schmutz, J.; Myers, R.M.; Butterfield, Y.S.N.; Krzywinski, M.I.; Skalska, U.; Smailus, D.E.; Schnerch, A.; Schein, J.E.; Jones, S.J.; Marra, M.A. "Generation and Initial Analysis of More Than 15,000 Full-Length Human and Mouse cDNA Sequences," *Proc. Natl. Acad. Sci. U.S.A.*, 2002, 99, 16899-16903.

Taylor, T.D.; Noguchi, H.; Totoki, Y.; Toyoda, A.; Kuroki, Y.; Dewar, K.; Lloyd, C.; Itoh, T.; Takeda, T.; Kim, D-W.; She, X.; Barlow, K.F.; Bloom, T.; Bruford, E.; Chang, J.L.; Cuomo, C.A.; Eichler, E.; FitzGerald, M.G.; Jaffe, D.B.; LaButti, K.; Nicol, R.; Park, H-S.; Seaman, C.; Sougnez, C.; Yang, X.; Zimmer, A.R.; Zody, M.C.; Birren, B.W.; Nusbaum, C.; Fujiyama, A.; Hattori, M.; Rogers, J.; Lander, E.S. and Sakaki, Y. "Human Chromosome 11 DNA Sequence and Analysis Including Novel Gene Identification," *Nature*, 2006, 440, 497-500.

Varki, A.; Cummings, R.; Esko, J.; Freeze, H.; Hart, G.; Marth, J. (eds.) *Essentials of Glycobiology, Cold Spring Harbor Laboratory Press*, 1999, Cold Spring Harbor, NY, 74-89.

Wallace, K.; Dasgupta, I.; Stratton, J.; Johnston, P.; Parry, R. "Letter to the Ediotr—Prevalence of the Antiheparin-Platelet Factor 4 Antibody in Hemodialysis (HD) Patients and Its Effects Upon Dialysis Access," *Clin. Nephrol.*, 2010, 74, 409-410.

Walz, D.A.; Wu, V.Y.; de Lamo, R.; Dene, H.; McCoy, L.E. "Primary Structure of Human Platelet Factor 4," *Thromb. Res.*, 1977, 6, 893-898.

Weinstein, P.S.; Skinner, M.; Sipe, J.D.; Lokich, J.J.; Zamcheck, N.; Cohen, A.S. "Acute-Phase Proteins or Tumour Markers: The Role of SAA, SAP, CRP and CEA as Indicators of Metastasis in a Broad Spectrum of Neoplastic Diseases," *Scand. J. Immunol.*, 1984, 19, 193-198.

Woo, P.; Sipe, J.; Dinarello, C.A.; Colten, H.R. "Structure of a Human Serum Amyloid A Gene and Modulation of Its Expression in Transfected L Cells," *J. Biol. Chem.*, 1987, 262, 15790-15795.

Xiong, L.; Andrews, D.; Regnier, F. "Comparative Proteomics of Glycoproteins Based on Lectin Selection and Isotope Coding," *J. Proteome Res.*, 2003, 2, 618-625.

Yamada, Y.; Itano, N.; Narimatsu, H.; Kudo, T.; Hirohashi, S.; Ochiai, A.; Tohnai, I.; Ueda, M.; Kimata, K. "CD44 Varian/ Exon 6 Expressions in Colon Cancer Assessed by Quantitative Analysis Using Real Time Reverse Transcriptase-Polymerase Chain Reaction," *Oncol. Rep.*, 2003, 10, 1919-1924.

Yang, Z.; Harris, L.E.; Palmer-Toy, D.E.; Hancock, W.S. "Multilectin Affinity Chromatography for Characterization of Multiple Glycoprotein Biomarker Candidates in Serum From Breast Cancer Patients," *Clin. Chem.*, 2006, 52, 1897-1905.

(56) References Cited

OTHER PUBLICATIONS

Zhang, X.; Chen, L.; Bancroft, D.P.; Lai, C.K.; Maione, T.E. "Crystal Structure of Recombinant, Human Platelet Factor 4," *Biochemistry*, 1994, 33, 8361-8366.

Hillenkamp, F. and Karas, M., "Mass Spectrometry of Peptides and Proteins by Matrix-Assisted Ultraviolet Laser Desorption/Ionization," *Methods in Enzymology*, 1990, 193, pp. 280-295.

Qiu, R. and Regnier F.E. "Use of Multidimensional Lectin Affinity Chromatography in Differential Glycoproteomics," *Anal. Chem.*, 2005, 77, pp. 2802-2809.

Pan, C. et al., "Robust Estimation of Peptide Abundance Ratios and Rigorous Scoring of Their Variability and Bias in Quantitative Shotgun Proteomics," Anal. Chem., 2006, 78, pp. 7110-7120.

\* cited by examiner

DETECTION OF GLYCOPEPTIDES AND GLYCOPROTEINS FOR MEDICAL DIAGNOSTICS

CROSS-REFERENCE TO RELATED APPLICATIONS

This invention claims priority to U.S. Provisional Patent Application Ser. No. 60/958,016, filed Jul. 2, 2007, which is herein incorporated by reference.

TECHNICAL FIELD

This invention relates to the field of glycoproteomics for medical diagnostic purposes.

BACKGROUND

Glycosylation is the process or result of addition of saccharides to proteins and lipids. It is a common co-translational or post-translational modification of proteins. The majority of proteins synthesized in the rough endoplasmic reticulum undergo glycosylation. It is estimated that more than half of all cellular and secretory proteins are glycosylated (Apweiler et al., 1999, *Biochim. Biophys. Acta* 1473: 4-8). Glycosylation is important for modulating normal cellular processes and recognition events. Changes in the carbohydrate moieties of the glycan also may change normal glycoprotein function. Aberrations, such as the changes in the amount of fucose, sialic acid, glucose, galactose, mannose, N-acetylgalactosamine, N-acetylglucosamine, a Lewis antigen, or N-linked β(1,6)-branching in the glycan portion of the core glycan, have been observed in several disease processes, including cancer. In mammals, over-expression of fucosyltransferases leading to increased fucosylation of cell surface glycoproteins has been correlated with malignancy and increased metastatic potential in breast, liver, lung, and ovarian cancer. Because the tumor-associated fucosylated or Lewis antigen containing proteins are often liberated from the cell surface and can be detected in the blood stream (Orntoft and Vestergaard, 1999, *Electrophoresis* 20: 362-371), pathological changes are likely to be reflected in serum protein profiles. While previous studies have reported increased fucosylation or sialylation of Lewis antigens on specific proteins isolated from serum of cancer patients, these single proteins are often non-specific and are present in other types of disease or neoplasia.

Presently, diseases are largely diagnosed, and patient status is monitored, through the use of clinical chemistry analyses and/or analyses of individual proteins. By and large, these are not as specific or as sensitive as is desirable. For example, while serum concentrations of prostate specific antigen (PSA) are used for the detection of prostate cancer and for monitoring its recurrence following treatment, this technique is not very sensitive, has a high rate of false positives, and the PSA serum concentrations do not correlate with the seriousness of the cancer. Similarly, the serum activity of alanine aminotransferase (ALT) is used to detect and monitor liver damage. While widely used, usefulness of this approach is limited because an increase in serum ALT activity does not give an indication of what is causing the liver damage, and significant damage to the liver can occur before the increase in serum ALT activity, thus ALT activity cannot always be used reliably to monitor liver damage.

Protein biomarker profiling holds the promise of enabling increased diagnostic and prognostic monitoring of disease, treatment efficacy, and general health. Current methods to detect the presence of protein biomarkers associated with a specific disease state include separating proteins by their mass (SDS-PAGE), charge (isoelectric focusing and 2-D gel electrophoresis) and immunoreactivity (ELISA). While these techniques allow qualitative or quantitative detection of a particular biomarker, use of these methods in discovering novel biomarkers is hindered by insufficient sensitivity, specificity, lack of quantitative measurement, and/or they are time intensive. Finally, many types of cancers and other diseases currently have no clinically useful biomarkers.

Mass spectrometry-based strategies for protein identification and quantification have made it possible to perform global, large scale comparative proteomics in complex biological samples. However, current methods in proteomics are generally inadequate for the study of glycoproteins. Two-dimensional gel electrophoresis is not rapid enough for routine diagnostic use. Multidimensional chromatographic methods suffer in that changes in glycosylation have little impact on retention time in reversed phase chromatography. Of importance for diagnostics, existing methods for quantifying significant disease-related differences in glycosylation are unsatisfactory, particularly at a high throughput proteomics level.

The merits of targeting glycans as a way to identify proteins might seem unusual. The logic behind this strategy stems from the fact that in the case of glycoproteins, glycan structure often changes in association with disease (Yamada et al., 2003, *Oncol. Rep.* 10: 1919-1924). The fact that these aberrant glycans can also be immunogenic has been exploited by pathologists in detecting cancer. Through the use of fluorescently labeled glycan-directed antibodies, staining procedures have been developed that allow differentiation between normal and malignant cells in tissue on the basis of targeting aberrant glycosylation (Edwards et al., 1986, *Cancer Res.* 46: 1306-1317). In addition, surface glycoproteins are well documented to play a prominent role in the loss of cellular adhesion, metastasis, the binding of tumor cells at remote sites, and secondary tumor colonization. For example, the Lewis (Le) antigens a ($Le^a$), b ($Le^b$), x ($Le^x$), and y ($Le^y$), and their sialylated forms s-$Le^a$, s-$Le^b$, s-$Le^x$, and s-$Le^y$, are among the more important glycans involved in these processes (Brockhausen, 2006, *EMBO Rep.* 7: 599-604). Cancer-associated glycoproteins carrying these glycans have been reported to be shed into blood and lymph as well (An et al., 2006, *J. Proteome Res.* 5: 1626-1635). Unfortunately, the proteins associated with cancer-associated glycans are generally unknown. If suitable analytical methods were developed and the structures of the glycoproteins were determined, they could potentially be used as cancer biomarkers.

The value of affinity selection in glycoprotein identification has been well established with lectins (Drake et al., 2006, *Mol. Cell. Proteomics* 5: 1957-1967). Immobilized lectins that seek out disease-related features of glycans reduce the complexity of blood samples sufficiently so that glycoproteins can be identified by shotgun proteomics without abundant protein removal (Rosenfeld et al., 2007, *J. Biochem. Biophys. Methods* 70: 415-426). Glycoproteins have also been identified through affinity selection of their glycopeptides from tryptic digests (Xiong et al., 2003, *J. Proteome Res.* 2: 618-625). After deglycosylation of the affinity selected glycopeptides are further fractionation by RPC, peptides carrying the glycan binding site can be identified by tandem mass spectrometry (Qiu and Regnier, 2005, *Anal. Chem.* 77: 7225-7231).

Present testing for cancer and other diseases relies on testing serum for the concentrations of single proteins which are loosely correlated to the disease, or for the activities of serum enzymes which are generally indicative of abnormal function of one or more organs. Increases in both the specificity and sensitivity over these current tests would greatly improve the accuracy and timeliness of the diagnosis and allow improved treatment selection and patient monitoring. New, more sensitive and specific markers of diseases, in particular cancers, are needed. The invention described here addresses these and related needs.

BRIEF SUMMARY OF THE INVENTION

Methods for detecting the presence or absence of diseases in subjects are provided, which include providing a means to determine one or more of the following: (i) status of the subject, (ii) status of the disease, (iii) response of the subject to the disease, (iv) response of the disease to treatment, and (v) the general health status of the subject. As an example, the presence or absence of a cancer such as lymphoma, remission of the cancer, and its subsequent reoccurrence can be monitored along with the status of the patient. As another example, glycan-targeting antibodies may be used to identify cancer-associated glycoproteins in plasma of breast cancer patients.

Methods for detecting the presence, absence, progression, regression, or extent of a disease or disorder in a subject are provided, which include: (a) obtaining two or more sample glycopeptides or glycoproteins from the subject; (b) obtaining two or more reference glycopeptides or glycoproteins; (c) comparing the sample glycopeptides or glycoproteins with the reference glycopeptides; and (d) detecting a difference in glycosylation state between the sample glycopeptides or glycoproteins and the reference glycopeptides or glycoproteins, which difference is indicative of the presence, absence, progression, regression, or extent of the disease or disorder in the subject. The comparison of sample glycopeptides or glycoproteins with reference glycopeptides or glycoproteins may include using global internal standard technology (GIST) with mass spectral detection, liquid chromatography with absorbance of fluorescence detection, capillary electrophoresis with absorbance or fluorescence detection, or an immunological array in which detection is achieved by surface plasmon resonance, interferometry, or fluorescence. For example, comparing the sample glycopeptides or glycoproteins with the reference glycopeptides or glycoproteins may include using isotopically labeled internal standard peptides and mass spectrometry, it may include using global isotopic coding of glycopeptides or glycoproteins and mass spectrometry, may include using liquid chromatography and absorbance or fluorescence, or may include immunological assaying of biomarkers from test subjects and disease-free subjects. The glycosylation state may relate to the amount of fucose, sialic acid, glucose, galactose, mannose, N-acetylgalactosamine, N-acetylglucosamine, a Lewis antigen, or N-linked $\beta(1,6)$-branching in the glycan core. Thus, for example, the glycosylation state may be one or more of fucosylation, sialylation, glucosylation, galactosylation, N-acetyl galactosylation, N-acetyl glucosylation, or mannosylation. In one preferred example, the glycosylation state is either fucosylation, a Lewis antigen, or both. The methods may include affinity selecting glycopeptides or glycoproteins using either lectins or antibodies. The disease assayed for may be cancer. The glycopeptides or glycoproteins may include four consecutive residues of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9.

Methods for detecting the presence, absence, progression, regression, or extent of a disease or disorder in a subject are provided, which include: (a) obtaining two or more sample glycopeptides or glycoproteins from the subject; (b) obtaining two or more reference glycopeptides or glycoproteins; (c) comparing the sample glycopeptides or glycoproteins with the reference glycopeptides; and (d) detecting a difference in concentration between the sample glycopeptides or glycoproteins and the reference glycopeptides or glycoproteins; where a difference in concentration between the sample glycopeptides or glycoproteins and the reference glycopeptides or glycoproteins is indicative of the presence, absence, progression, regression, or extent of the disease or disorder. The difference in the concentration of glycopeptides or glycoproteins may be due to one or more changes in glycopeptide or glycoprotein mass. The change in concentration of glycopeptides or glycoproteins may be due to a change in the amount of fucose, sialic acid, glucose, galactose, mannose, N-acetylgalactosamine, N-acetylglucosamine, Lewis antigen, or N-linked b(1,6)-branching in the glycan portion of the glycoconjugate. The change in concentration of glycopeptides or glycoproteins may be due to one or more monosaccharides such as fucose, galactose, N-acetylgalactosamine or sialic acid or an antigenic glycan.

Methods for detecting the presence, absence, progression, regression, or extent of a disease or disorder in a subject are provided, which include: (a) obtaining test glycopeptidic or glycoproteomic profiles from the subject; (b) obtaining reference glycopeptidic or glycoproteomic profiles; (c) comparing the test glycopeptidic or glycoproteomic profiles with the reference glycopeptidic or glycoproteomic profiles; and (d) detecting difference in the glycosylation state between the test glycopeptidic or glycoproteomic profiles and the reference glycopeptidic or glycoproteomic profiles, which difference is indicative of the presence, absence, progression, regression, or extent of the disease or disorder in the subject. In one preferred example, the glycosylation state is fucosylation. The disease assayed for may be cancer.

Methods are provided for diagnosing diseases, which include the steps of: (a) providing samples which comprise at least two glycopeptides or glycoproteins; (b) providing references which comprise at least two glycopeptides or glycoproteins; and (c) comparing the concentration of the sample glycopeptides with the concentration of reference glycopeptides. A difference in the concentration between the sample glycopeptides or glycoproteins and the reference glycopeptides or glycoproteins is an indicator of the disease. In the practice of the methods, the concentration may be a change in glycopeptide or glycoprotein mass, absorbance, or fluorescence. The methods generally include affinity selecting the glycopeptides using one or more lectins or antibodies. The methods may include detecting changes in the glycosylation state of at least one glycopeptide or glycoprotein. Changes in concentration may be detected by measuring the amount of in the amount of fucose, sialic acid, glucose, galactose, mannose, N-acetylgalactosamine, N-acetylglucosamine, Lewis antigen, or N-linked $\beta(1,6)$-branching in the glycan portion of the glycopeptides or glycoproteins. In one preferred example, the change in concentration is detected by detecting changes in fucosylation. The disease assayed for may be cancer. The glycopeptides or glycoproteins may include four consecutive residues of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9.

Purified glycopeptides or glycoproteins are provided, which include four consecutive residues of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9, where the glycopeptides are breast cancer biomarkers.

DETAILED DESCRIPTION OF THE PREFERRED EMBODIMENTS

Figure 1:
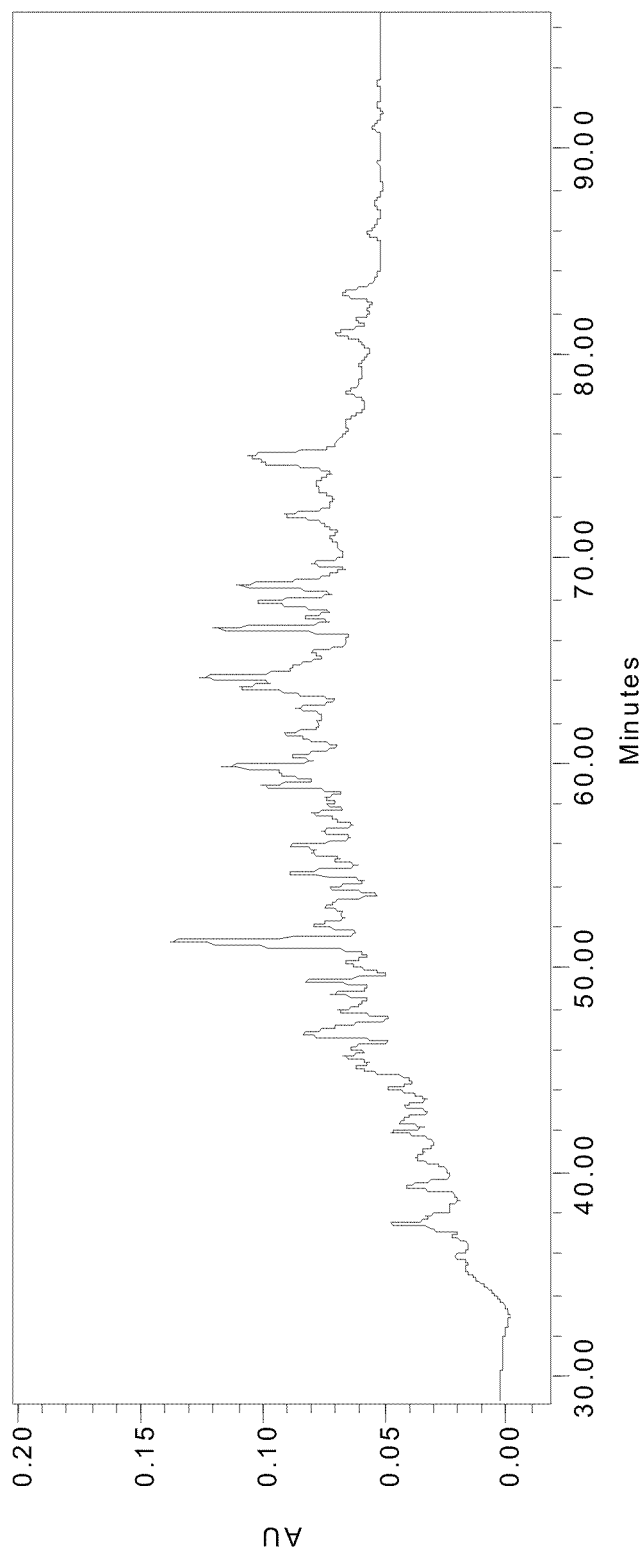
FIG. 1 is a graph depicting a reversed-phase chromatogram of *Lotus tetragonolobus*-affinity selected peptides.

Unless defined otherwise, all technical and scientific terms used herein have the meaning commonly understood by a person skilled in the art to which this invention belongs. A general review of glycobiology is given in *Essentials of Glycobiology*, 1999, Varki et al., eds., Cold Spring Harbor Laboratory Press, Cold Spring Harbor, N.Y., which is herein incorporated by reference.

Glycoproteomics methods are provided that may be used to detect and quantify a desired set of glycosylated peptides (glycopeptides) or glycosylated proteins (glycoproteins) in a subject for the purpose of diagnosis and monitoring the presence, absence, progression, regression, or extent of a disease such as, for example, cancer. Methods for isolation of glycosylated peptides (glycopeptides) and/or glycosylated proteins (glycoproteins) and their quantification for the purpose of monitoring onset or appearance of a disease are provided. In the practice of this invention, a variety of glycopeptides may be analyzed, including N-linked glycosylated peptides or glycosylated proteins and O-linked glycosylated peptides or glycosylated proteins. Examples of glycosylation states useful for practicing the present invention include fucosylation, sialylation, glucosylation, galactosylation, mannosylation, and antigen conjugation to existing glycan structures. In one example, the glycosylated peptides or glycosylated proteins may be fucosylated peptides or proteins. One or more glycosylation states may be detected in the practice of the present invention. In some embodiments, the difference in glycosylation state may occur due to one or more structural changes that may cause a change in peptide or protein mass. Changes in glycosylation state may result from an aberration in core glycan structure. Examples of changes in glycosylation state include those resulting from changes in the amount of fucose, sialic acid, glucose, galactose, mannose, N-acetylgalactosamine, N-acetylglucosamine, a Lewis antigen, or N-linked β(1,6)-branching on the glycoconjugates such as glycopeptides or glycoproteins.

"Glycan" refers to the carbohydrate portion of a glycoconjugate, such as a glycopeptide, glycoprotein, glycolipid, or proteoglycan. It is contemplated that the methods of the present invention may be practiced with any glycoconjugates, including glycosylated peptides (glycopeptides), glycosylated proteins (glycoproteins), glycosylated lipids (glycolipids), and proteoglycans. Generally, glycans tend be oligosaccharides or polysaccharides.

A "glycoform" of a protein of unique primary, secondary, tertiary, and quaternary structure with a glycan of specific structure attached. It is often the case that a single glycoprotein can have 20-50 glycoforms, all based on differences in the glycan portion of the glycoprotein. A glycoprotein with many glycoforms is often referred to as being "microheterogeneous" in glycosylation.

The "glycoproteome" is the entire complement of glycosylated proteins expressed by a genome, cell, tissue, organ, or organism. More specifically, it refers to the expressed glycosylated proteins at a given time point under defined conditions.

While reference is made to glycosylated peptides, glycosylated polypeptides and glycosylated proteins also are contemplated. Glycopeptides are typically obtained by enzymatic or chemical cleavage of glycoproteins. Conversely, glycoproteins can readily be identified through affinity selection of their glycopeptides from tryptic digests. Thus, reference to "glycosylated peptide" or "glycopeptide" is meant to specifically also include the terms "glycosylated polypeptide," i.e., "glycopolypeptide" or "glycosylated protein," i.e., "glycoprotein". In some embodiments, the glycopeptides have between three and twenty amino acid residues, and preferably they have four to ten residues.

The glycosylated peptides or glycosylated proteins may be labeled. Labeling of peptides can be accomplished using a variety of techniques known in the art, in vivo or in vitro, including, but not limited to, isotope-coded affinity tagging, stable isotope labeling of amino acids in cell culture (SILAC), isobaric tagging for relative and absolute quantification (iTRAQ), ICAT labeling, labeling using fluorinated affinity tags, amino-terminal sulphonation, dimethyl labeling, global internal standard technology (GIST), $^{16}O/^{18}O$ labeling, or labeling using mixtures thereof. One of the methods of the present invention includes labeling all peptide fragments. This is preferably accomplished using the global internal standard technology (GIST) method, which employs acetate and tri-deuteroacetate as coding agents. Methods for labeling peptides are disclosed in, for example, U.S. Pat. Nos. 6,864,099 and 6,872,575; in Asara et al., 2006, *Nature Protocols* 1: 46-51; Chakraborty and Regnier, 2002, *J. Chromatography* 949: 173-184; and in Julka and Regnier, 2005, *Briefings in Functional Genomics and Proteomics* 4: 158-177, all of which are incorporated herein by reference. The glycopeptides may also be selected and identified without labeling.

Another method by which glycoproteins can be identified and quantified is through 2-dimensional chromatography. Glycoproteins are affinity selected with an immobilized lectin or antibody column in the first dimension and subsequently transferred to a reversed phase chromatography (RPC) column for second dimension resolution. Resolved glycoproteins or glycopeptides eluting from the RPC column are quantified by absorbance and fraction collected for mass spectral analysis in cases where they are to be identified. When higher detection sensitivity is needed all proteins in a blood sample are first tagged with an affinity label before fractionation. Glycoprotein detection during elution from the RPC is by fluorescence in this case.

The glycosylated peptides or glycosylated proteins may be isolated or purified from the sample. Isolation of glycosylated peptides or glycosylated proteins may be performed, for example, using affinity chromatography. Preferably, the glycosylated peptides or glycosylated proteins are isolated using a lectin or antibody affinity selector. More preferably, the lectin used for affinity purification for fucosylated peptides is obtained with a fucose targeting lectin such as *Lotus tetragonolobus* lectin (LTL). The more preferable antibodies target one of the Lewis antigens. The sample that is assayed may be obtained from the subject's serum, urine, sputum, cerebral spinal fluid, bronchial secretions, or other tissues. Moreover, both the sample glycopeptides and the reference glycopeptides may be obtained from the same subject; for example, they may be obtained from the subject at different times.

In the practice of the present invention, the amount or concentration of glycosylated peptides or glycosylated proteins may be quantified. As well, changes in the glycosylated peptides or glycosylated proteins may be quantified. The changes in these peptides are preferably quantified using Global Internal Standard Technology (GIST) stable isotope labeling. Other ways of quantification of the glycosylation states and/or concentration of glycoconjugates include changes in peptide or biomarker mass, absorbance, or fluorescence relative to a chemically identical reference substance. One example of the difference in the concentration of glycopeptides or glycoproteins is a difference due to a change in peptide or protein mass. For example, the change in concentration of glycopeptides or glycoproteins may be due to a change in the amount of one or more of the following; fucose, sialic acid, glucose, galactose, mannose, N-acetylgalactosamine, N-acetylglucosamine, Lewis antigen, or N-linked b(1,6)-branching in the glycan portion of the glycoconjugates (for example, glycopeptides or glycoproteins). In other embodiments, the comparison of the sample glycopeptides or glycoproteins with the reference glycopeptides or glycoproteins may include using one or more of global internal standard technology (GIST) with mass spectral detection, liquid chromatography with absorbance of fluorescence detection, capillary electrophoresis with absorbance or fluorescence detection, or an immunological array in which detection is achieved by surface plasmon resonance, interferometry, or fluorescence. The methods may include affinity selecting the glycopeptides or glycoproteins using either lectins or antibodies. Concentration differences in glycoproteins are generally sensed by changes in absorbance of proteins eluting from a liquid chromatography column.

In one example of the present invention, a global analysis of glycosylated peptides in serum from a subject may be performed. The analysis may include assessing changes in two or more peptides bearing potentially aberrant glycosylation or from other peptides in protein biomarkers. Changes in peptides disease associated changes in glycosylation may be assessed in a variety of test subjects, for example healthy subjects or unhealthy subjects, in subjects performing routine health maintenance examinations, in subjects undergoing preventative treatment against diseases, in subjects undergoing treatment for diseases, and in subjects whose diseases are in remission, or in relapse.

In another example of the present invention, glycan-targeting antibodies find utility in simplifying glycoprotein mixtures while still capturing disease-associated proteins of widely differing structure, thereby providing a way to recognize disease-related makers. In one example, the disease may be cancer, and the antibody may be specific for Le$^x$ antigen (Rabina et al., 1997, *Anal. Biochem.* 246: 71-78). In one embodiment of the methods of the present invention, blood plasma samples from human subjects may be applied directly to IAC columns. Following dissociation of the immune complex on the immunosorbent with an acidic mobile phase, glycoproteins are eluted and collected as a single fraction. Proteins thus selected are then identified by conventional proteomics methods (McDonald and Yates, 2002, *Dis. Markers* 18: 99-105).

The terms "subject" or "patient" refer to vertebrate animals, and especially to humans and nonhuman animals, including dogs, sheep, horses, cows, rats, birds, reptiles, fish, etc. Preferably, the subject is a human. The subject may be healthy or unhealthy. A sample from the subject may be obtained once. Alternatively, samples from the subject may be obtained more than once.

The methods of this invention may be practiced in clinically normal subjects or with a variety of diseases, to monitor the presence or absence of the disease. As used herein, monitoring the presence or absence of a disease refers to the monitoring of the presence, absence, nature, progression, regression, evaluation, diagnosis, or extent of a disease, disorder, or condition in a subject. Thus, the diagnostics methods of the present invention can be used to test for the presence or absence (i.e., to monitor the presence, absence, nature, progression, regression, evaluation, diagnosis, or extent) of a wide variety of diseases or disorders, including but not limited to neoplastic (cancer), bacterial, viral, prion-caused, nutritional, endocrine, and toxic diseases. The methods of the present invention may be practiced pre-, during-, and post-disease or disorder occurrence. As well, the methods of the present invention may be practiced pre-, during-, and post-disease or disorder treatment.

In one application, the disease is cancer. The methods and compositions of the present invention are suitable for diagnosing, for example, a variety of cancers, including breast, ovary, testicular, prostate, lung, colon, kidney, stomach, bone, thyroid, hematopoietic, pancreas, liver, bladder, melanoma, lymphoma, leukemia, central nervous system tumors, or tumors of mesothelial, endothelial, or epithelial origin in mammals, including humans. In particular the methods and the compositions are suitable for diagnosing a lymphoma or for diagnosing breast cancer. It is contemplated that the quantitative signatures of the glycoconjugates according to present invention will vary between different types of cancer.

Changes in glycopeptides or glycoproteins may be assayed at different times, for example in a healthy subject, to monitor the possible appearance of a disease, for example cancer; in a subject with a disease, to monitor the progress of the disease; in a subject with a disease undergoing treatment, to assess the influence of the treatment on the disease; to assess the influence of treatment on the subject; and post-treatment, to monitor for any possible relapse of the disease. For example, the subject may be a subject with lymphoma. When the method is used with a subject with lymphoma who is treated (for example with chemotherapy, radiotherapy, or immunotherapy), changes in fucosylated peptides may be assessed in the subject pre-treatment, during-treatment, post-treatment (remission), and later, in case of a possible relapse of the cancer. In another example, the subject may be a subject with breast cancer. When the method is used with a subject with breast cancer who is treated (for example with chemotherapy, radiotherapy, or immunotherapy), changes in fucosylated peptides or proteins may be assessed in the subject pre-treatment, during-treatment, post-treatment (remission), and later, in case of a possible relapse of the cancer.

In one example, a stable isotope label, affinity selection, and glycoproteomics techniques may be used to isolate and quantify changes in fucosylated peptides or proteins associated with malignant lymphoma. Peptides that become elevated in a subject with a lymphoma may be detected. Thus, the method may be used in a serum-based proteomic analysis for discovering biomarkers of cancer, monitoring patient's response to therapy (such as chemotherapy, radiotherapy, immunotherapy, etc.), and indicating malignant lymphoma disease recurrence.

Changes in a glycopeptidic/glycoproteomic profile that includes a plurality of proteins associated with a certain disease state, or lack of disease, in a patient, also may be detected. As used herein, a "glycopeptidic profile" refers to at least two glycopeptides/glycoproteins that are obtained from a subject and that can be used to identify the presence or absence of a disease according to this invention. For example, a particular combination of a plurality of specific glycopeptides/glycoproteins (a "glycopeptidic profile" or a "profile") in a patient's sample may identify the absence of a disease, while another profile of the specific glycopeptides/glycoproteins may identify a disease state; yet a further profile of the specific glycopeptides/glycoproteins may identify the patient's body's response to the therapy, or the level of severity of recurrence or progression of disease (e.g., tumor size). Thus, various glycopeptidic profiles may be correlated with various states of the disease.

In a sample that is assayed, one or more of the glycopeptides/glycoproteins may be N-glycosylated. Alternatively, one or more of these glycopeptides/glycoproteins may be O-glycosylated. As well, a glycopeptidic profile may include any number of both N-glycosylated and O-glycosylated glycopeptides/glycoproteins.

In some embodiments, two or more glycopeptides obtained from a sample with two or more reference glycopeptides are compared for differences or changes. The amount or the type, i.e. character of glycosylation may be compared. The amount of glycosylation, such as fucosylation, branching, sialidation, etc., of at least two glycopeptides in the sample, as compared to the reference, may be correlated with the disease, disorder or condition. As well, the type, i.e., character of glycosylation may be associated with a particular disease. A variety of glycopeptides may be used, and these glycopeptides may be extracted from different cellular compartments. The glycopeptidic samples may include membrane glycopeptides, adhesion proteins, lectins, or mixtures thereof.

It is also possible to compare the masses of the sample glycopeptides with the masses of the reference glycopeptides. The change in peptide mass may be a decrease or increase in peptide mass. Thus, a percent change in one or more peptides with the same mass and MS/MS profile may be a diagnostic indicator of a disease or disorder. The change may reflect a percent increase in one or more peptides with the same mass and MS/MS profile or decrease in one or more peptides with the same mass and MS/MS profile. In one example, an increase of 50% or more in one or more peptides with the same mass and MS/MS profile may be an indicator of tumor presence. In another example, a decrease of 20% or more in one or more peptides with the same mass and MS/MS profile may be an indicator of tumor regression or treatment efficacy.

The sample obtained from a patient may represent a glycopeptidic profile of glycopeptides that are associated with a disease. The reference glycopeptidic profile may also be obtained from the subject being evaluated, but obtained at a different time. Alternatively, the reference glycopeptidic profile may be a composite glycopeptidic profile obtained from a plurality of subjects. As well, the reference glycopeptidic profile may be from a subject other than the subject being evaluated.

Not only can a disease be detected with increased sensitivity and specificity, but treatment of a disease can be more effectively evaluated by the ability to monitor progression or regression of a disease. In addition, treatment may be tailored to an individual patient by obtaining an individual glycopeptidic profile of the patient in a non-disease state (which may serve as a control profile) and comparing the control profile to profiles obtained during treatment of a disease.

Combinations of glycopeptides and glycoproteins may be used as signatures in the diagnosis, treatment, and monitoring of diseases and will thus be used in clinical, diagnostic, and discovery medicine. Thus, through the use of global glycoprotein analysis of plasma or serum and/or tissue samples, medical professionals and researchers may be provided with a way to diagnose a variety of diseases, guide treatment, and monitor a patient's physiological status. Early diagnosis of disease with information on the patient's physiological status will enable patient-directed treatment of disease in its early stages. Moreover, the methods may be used to monitor changes in the glycosylation state of proteins from any tissue. The methods may be practiced with any body fluid, but preferably with whole blood or blood plasma. For example, the proteins whose glycosylation state is monitored can be serum proteins. "Serum" refers to blood plasma from which clotting factors have been removed. Plasma is preferred over serum in analysis because the clotting process may have removed or damaged some biomarkers. This technology greatly increases the specificity and sensitivity of serum tests for many types of cancer and for many other diseases. The application of this method is global, in that it can test for alterations in all serum glycoproteins simultaneously.

The methods may be used to identify glycopeptides that are important in a variety of diseases such as cancer, infectious diseases, and metabolic diseases such as diabetes. Identification of glycopeptides that are diagnostic for specific diseases will greatly increase the understanding of the development of those diseases and will lead to more specific treatments for them. The methods of the present invention can permit regular (for example yearly check-up) testing of a patient's serum for markers of cancer and other diseases while they are still early in their development when therapy would be most effective. If afflicted by an active disease process, a blood test from a blood sample can be used to diagnose the disease, possibly identify the causative agent (bacterium, parasite, fungus, prion, or virus), evaluate the patient's status, and direct specific treatment based on the individual patient's overall profile. As well, samples from a given subject can be assayed with any desired frequency, for example daily, weekly, monthly, etc.

It is contemplated that the methods of the present invention are generally applicable to a wide variety of glycopathologies. In one embodiment, a serum-based glycoproteomics technique can be used to isolate and quantify changes in fucosylated peptides related to identifiable disease states in lymphosarcoma (lymphoma). It is possible to identify alterations in the glycosylation state of at least 46 peptides derived from the serum proteome. Corresponding to these glycopeptides, potential biomarkers can be isolated and identified in order to develop a diagnostic/prognostic test to monitor lymphosarcoma. Thus, in one example, combinations of fucosylated peptides may be used to identify lymphoma, monitor response of the patient to chemotherapy (remission), and indicate recurrence of the cancer.

In another embodiment, immunoaffinity chromatography may be used to isolate and identify breast cancer biomarker glycoproteins by targeting breast cancer-associated glycans. Overexpression of Le$^x$ antigen in breast cancer facilitates metastasis by promoting tumor cell adhesion at remote sites (Monzavi-Karbassi et al., 2005, *Int. J. Cancer* 117: 398-408). Thus, a unique group of Lewis antigen-bearing proteins may occur in breast cancer patients. These aberrant glycan bearing proteins may be used to identify the presence of breast cancer, monitor response of the patient to chemotherapy (remission), and indicate recurrence of the cancer. Using these approaches, there is not only the potential to discover serum markers of diseases such as cancer, but also to monitor response of a patient to therapy (chemotherapy, radiotherapy, immunotherapy, etc.), and to indicate recurrence of the disease.

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

EXAMPLE 1

Quantification of Stable Isotope-Labeled, Affinity Selected Glycopeptides for Diagnosis of Lymphoma This is an example of using a stable isotope label, affinity selection, and glycoproteomics techniques to isolate and quantify changes in fucosylated peptides associated with canine malignant lymphoma. Using this approach, 46 glycopeptides were found to be elevated in serum from a dog with lymphoma. The same 46 glycopeptides decreased following chemotherapy when the dog was in clinical remission and subsequently increased during relapse of the cancer. When the pre-chemotherapy serum of this and two other dogs with lymphoma were analyzed and compared to normal serum, there were 22 similar peptides identified, of which 19 glycopeptides were increased with lymphoma. These glycopeptides may be used as biomarkers of cancer, monitoring patient response to chemotherapy, and indicating disease recurrence.

Samples.

Normal, pooled canine serum (male, mixed breed, mixed age) was obtained from Harlan Bioproducts for Science (Indianapolis, Ind.). Samples from three dogs with naturally-occurring lymphoma (see Table 1) were obtained from left-over serum following clinical evaluation and before treatment at the Purdue University School of Veterinary Medicine.

TABLE 1

Canine Sample Information‡

| Case No. | Signalment† |
|---|---|
| 1 | 5-y-old, MN; Mixed breed |
| 2 | 6-y-old, MN; Terrier |
| 3 | 5-y-old, FS; Retriever |

†M = Male, N = Neutered, F = Female, S = Spayed
‡Samples obtained from serum left-over after clinical chemistry evaluation Malignant lymphoma is the most common cancer of the blood in dogs (Lucas et al., 2004, *J. Amer. Anim. Hosp. Assoc.* 40: 292-299). In this example, lymphoma in dogs was diagnosed based on clinical presentation, physical examination, and examination of neoplastic cells from enlarged lymph nodes. Serum samples pre-chemotherapy treatment (pre-treatment), post-chemotherapy treatment (post-treatment; while in remission), and post-chemotherapy treatment, during cancer relapse, were obtained from case No. 1. Pre-chemotherapy treatment serum samples were received from cases Nos. 2 and 3.

Materials.

Acetic-$d_0$-anhydride, acetic-$d_6$-anhydride, α-cyano-4-hydroxycinnamic acid, angiotensin II, bradykinin, ACTH fragment 18-39, P$_{14}$R, insulin oxidized β-chain, cysteine, dithiothreitol (DTT), endoglycopeptidase-F (PNGase F), L-fucose, N-hydroxysuccinimide, iodoacetic acid, phosphate buffered saline tablets (PBS), sodium phosphate, L-1-tosylamide-2-phenylethyl chloromethyl ketone (TPCK)-treated trypsin, N-tosyl-L-lysine chloromethyl ketone (TLCK), trifluoroacetic acid (TFA), and urea (molecular biology grade) were purchased from Sigma-Aldrich (St. Louis, Mo.). Agarose-bound *Lotus tetragonolobus* lectin (LTL) was purchased from Vector Laboratories, Inc. (Burlingame, Calif.). Sodium chloride (NaCl) was obtained from EMD Chemicals, Inc. (Gibbstown, N.J.). HPLC grade acetonitrile (ACN), calcium chloride (CaCl$_2$), HPLC grade hexane, manganese chloride (MnCl$_2$), and HPLC grade water were purchased from Mallinckrodt Baker, Inc. (Phillipsburg, N.J.). Bicinchoninic acid (BCA™) protein assay kits used in these experiments were purchased from Pierce Biotechnology, Inc. (Rockford, Ill.).

Protein Quantitation.

Serum protein concentrations were determined by the BCA™ protein assay. Samples were diluted 1:40 in PBS and analyzed according to the manufacturer's protocol. The average protein concentration was quantified based on the average of duplicate analyses.

Proteolysis.

A 1 mL aliquot of serum from normal, pre-treatment (lymphoma), post-treatment (remission), or relapse samples were incubated with 8 M urea for 30 minutes at room temperature. The disulfide bonds of the serum proteins were reduced by addition of DTT to a final concentration of 20 mM and incubated at 37° C. for 2 hours. Iodoacetic acid was then added at an iodoacetic acid to protein ratio of 1:10 and incubated in darkness on ice for an additional 2 hours. This alkylation reaction was then quenched by addition of cysteine (0.5 μg cysteine to 5 μg serum protein) and the sample was diluted to 1 M urea with PBS (pH=7.5). Proteolysis was achieved by incubating the samples for 24 hours at 37° C. in the presence of TPCK-treated trypsin at a trypsin to protein ratio of 1:25. Trypsinization was terminated by adding TLCK in a 2-fold molar excess to that of trypsin.

Synthesis of N-Acetoxy-$d_0$-Succinimide and N-Acetoxy-$d_3$-Succinimide (GIST).

The GIST isotope labeling reagents were made in accordance with a previously published protocol (Ji et al., 2000, *J. Chromatogr. B.* 745:197-210). A 1.77 g (15.4 mM) sample of N-hydroxysuccinimide was added to 5.0 mL (46.2 mM) of acetic-$d_0$-anhydride or acetic-$d_6$-anhydride. Both solutions were stirred for 15 hours at room temperature. The resultant white crystalline products were washed extensively with hexane and dried under vacuum.

Isotopic Labeling of Peptides.

A 3-fold molar excess of N-acetoxy-$d_0$-succinimide ($d_0$) or N-acetoxy-$d_3$-succinimide ($d_3$) was added to equal aliquots (equivalent protein concentrations) of the peptide solutions. The respective GIST isotopic label used for each sample group is listed in Table 2. The samples were incubated at room temperature and the acetylation reaction was allowed to proceed for 15 hours. Following GIST labeling, equal aliquots (15 mg/mL each) of the two samples were mixed. The mixed samples were adjusted to pH 7-8 prior to affinity selection.

TABLE 2

GIST Isotope Labels Used for Each Sample Group

| Case No. | Sample Groups Compared | GIST Label[†] |
|---|---|---|
| 1 | Normal serum | $d_0$ |
|   | Pre-chemotherapy serum | $d_3$ |
| 1 | Pre-chemotherapy serum | $d_0$ |
|   | Post-chemotherapy serum | $d_3$ |
| 1 | Post-chemotherapy serum | $d_0$ |
|   | Relapse serum | $d_3$ |
| 2 | Normal serum | $d_0$ |
|   | Pre-chemotherapy serum | $d_3$ |
| 3 | Normal serum | $d_0$ |
|   | Pre-chemotherapy serum | $d_3$ |

[†]$d_0$ = N-acetoxy-$d_0$-succinimide, $d_3$ = N-acetoxy-$d_3$-succinimide

Lectin Affinity Selection.

Fucosylated peptides were affinity selected using agarose-bound *Lotus tetragonolobus* lectin (LTL). GIST-labeled peptides from serum samples were equilibrated with 10 mM sodium phosphate loading buffer (pH=7.0) containing 0.15 M NaCl, 0.01 mM $MnCl_2$, and 0.1 mM $CaCl_2$. Equivalent amounts of the mixed samples were loaded onto 4 mL of packed LTL agarose beads and allowed to incubate for 12 hours at room temperature with mixing. The LTL agarose beads were then washed with 10 column volumes of loading buffer to remove unbound peptides. In order to elute bound, fucosylated peptides, 2 mL of elution buffer (pH=5.0) containing 10 mM sodium phosphate, 0.15 M NaCl, 0.01 mM $MnCl_2$, 0.1 mM $CaCl_2$ and 200 mM L-fucose was added. The solution was incubated at room temperature for an additional 5 hours. The eluate containing the fucosylated peptides was collected for HPLC fractionation and MALDI-TOF analysis.

Deglycosylation by N-Glycosidase F (PNGase F).

The fucosylated peptides (pH 7.0) were deglycosylated in the presence of 2 µL (15 U) of PNGase F. This reaction mixture was incubated at 37° C. and allowed to proceed for 18 hours.

HPLC Fractionation of Peptides.

Peptides were fractionated using a reversed-phase, 250× 4.6 mm i.d. $C_{18}$ monomeric column (Grace Vydac, Hesperia, Calif.). HPLC separation of the fucosylated peptides was performed using a Waters HPLC system (Milford, Mass.) complete with two Waters 510 pumps and a 996 PDA detector. Prior to fractionation, the reversed-phase column was equilibrated using 100% mobile phase A (99.9% $H_2O$ with 0.1% TFA) at a flow rate of 1.00 mL/minute for 10 column volumes. After system equilibration, a 2 mL portion of the LTL-selected peptides was injected and separated with gradient elution. The gradient profile consisted of an initial 20 minutes at 100% mobile phase A and increasing linearly to 100% mobile phase B (80% acetonitrile and 19.9% $H_2O$ in 0.1% TFA) at 115 minutes. The mobile phase was maintained at 100% mobile phase B for 10 minutes, followed by a return to initial conditions (100% mobile phase A). Eluting peptides were monitored at 215 nm, manually collected, and concentrated to a final volume of 10 µL prior to analysis by MALDI-TOF mass spectrometry.

Figure 2:
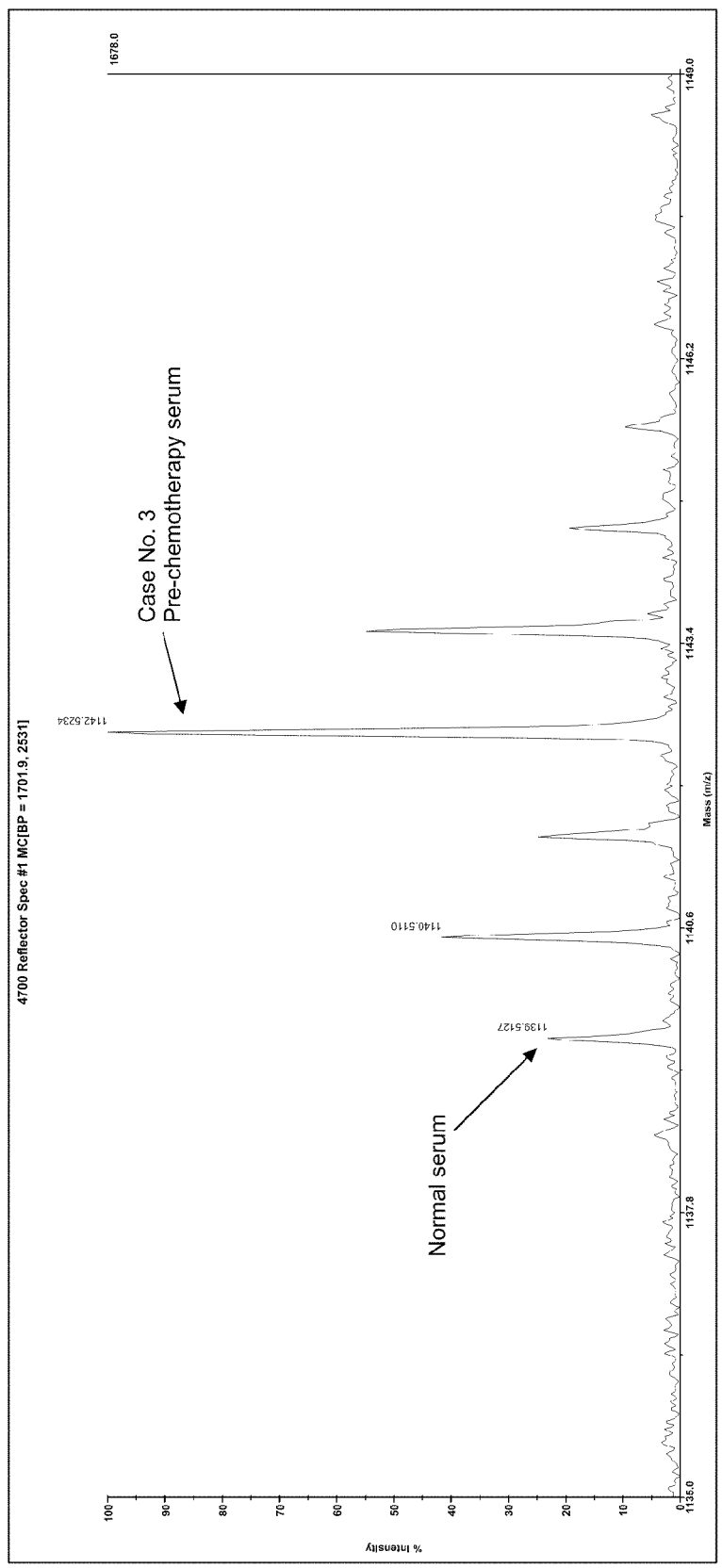
FIG. 2 is a graph of a MALDI-TOF MS spectrum of GIST-labeled glycopeptides.

FIG. 2 is a graph depicting a reversed-phase chromatogram of *Lotus tetragonolobus* affinity selected peptides. This is a reversed-phase chromatogram of peptides from case no. 1 (normal versus pre-chemotherapy treatment sera). These peptides are from GIST labeled fucosylated peptides that were selected using *Lotus tetragonolobus* lectin and deglycosylated with PNGase F. AU, absorbance units.

MALDI-TOF Mass Spectrometry.

The concentrated peptide fractions were reconstituted with 40 µL of 50% ACN:49.9% $H_2O$ in 0.1% TFA (v/v). A 1 µL volume of each sample was applied to the MALDI target and overlaid with 1 µL of α-cyano-4-hydroxycinnamic acid matrix (10 mg/mL in 50% ACN:49.9% $H_2O$ in 0.1% TFA (v/v)). MALDI-TOF mass spectrometry was performed on a Voyager 4700 (Applied Biosystems, Foster, Calif.). MALDI-TOF peptide masses were acquired in positive reflection mode at 20 keV accelerating voltage with an average of 1000 laser shots per spectrum. External calibration was performed using a mixture of standard peptides containing angiotensin II, bradykinin, ACTH fragment 18-39, $P_{14}R$, and insulin oxidized β-chain.

Quantitative Analysis by MALDI-TOF MS.

Figure 3:
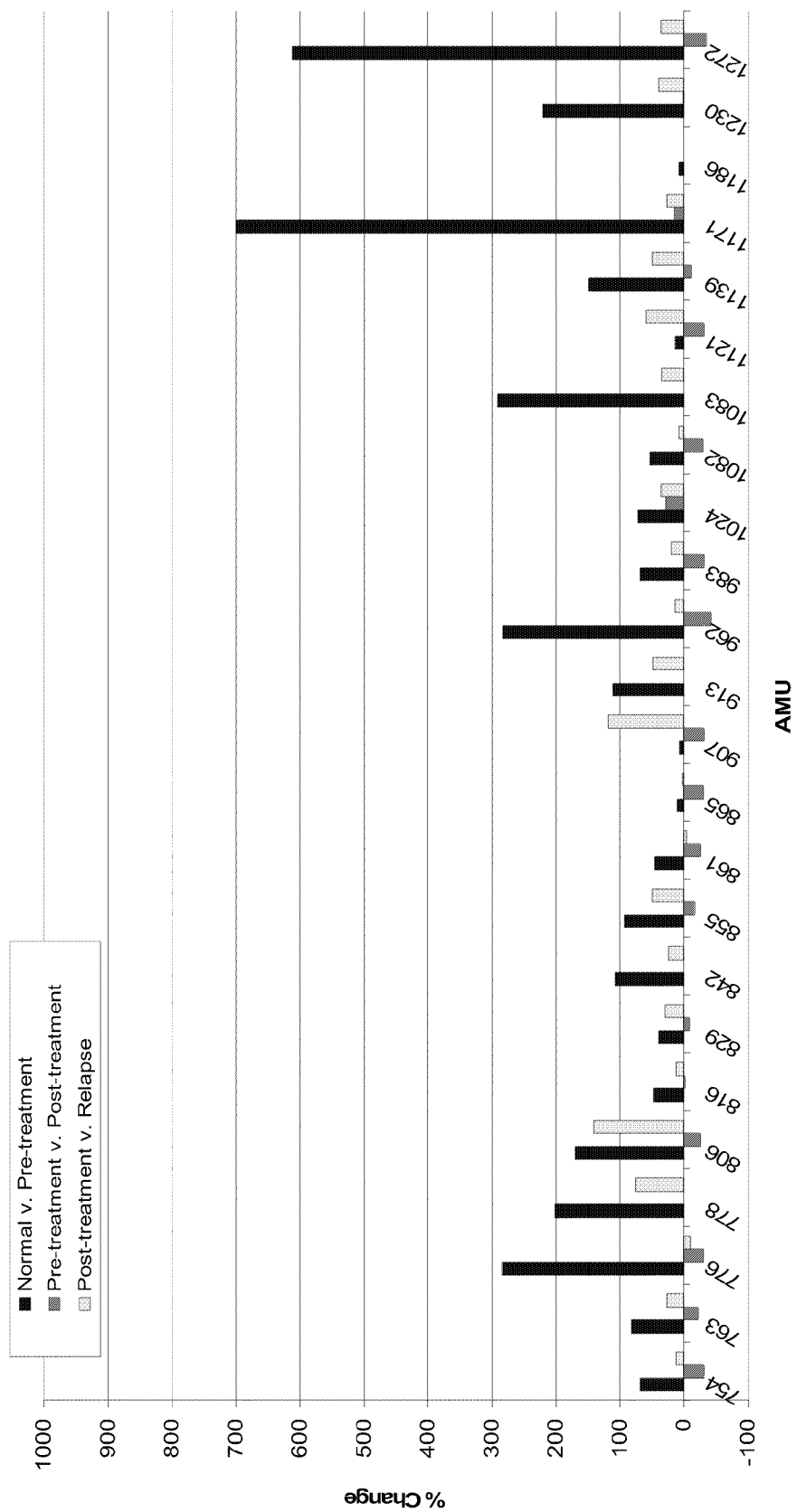
FIG. 3 (peptide masses 754 m/z to 1272 m/z) is a graph illustrating how specific, identifiable, and unique peptide masses changed predominantly with lymphoma (Pre-treatment), decreased after a chemotherapy treatment (Post-treatment, remission), and increased with recurrence of lymphoma (Relapse).

Changes in fucosylated peptides were quantitated using MALDI-TOF mass spectrometry by calculating the percent change of the relative intensities between the $d_0$ and $d_3$ labeled samples. FIG. 3 illustrates a MALDI-TOF MS spectrum of GIST-labeled peptides. This is a MALDI-TOF MS spectrum of differentially labeled peptides from normal dog serum and serum from a dog with lymphoma (case No. 3). These samples, containing both $d_0$ and $d_3$ labeled peptides, appear in the mass spectrum as a doublet and are separated by 3 amu (atomic mass units; FIG. 3). The peptide indicated with the peak at 1139 m/z was present in a higher concentration in the dog with lymphoma when compared to this peptide in the normal serum. Because the GIST labeling reagents can also acetylate the primary amino group in lysine, the mass difference between control and experimental samples can increase an additional 3 amu or 6 amu in lysine-containing peptides.

Figure 4:
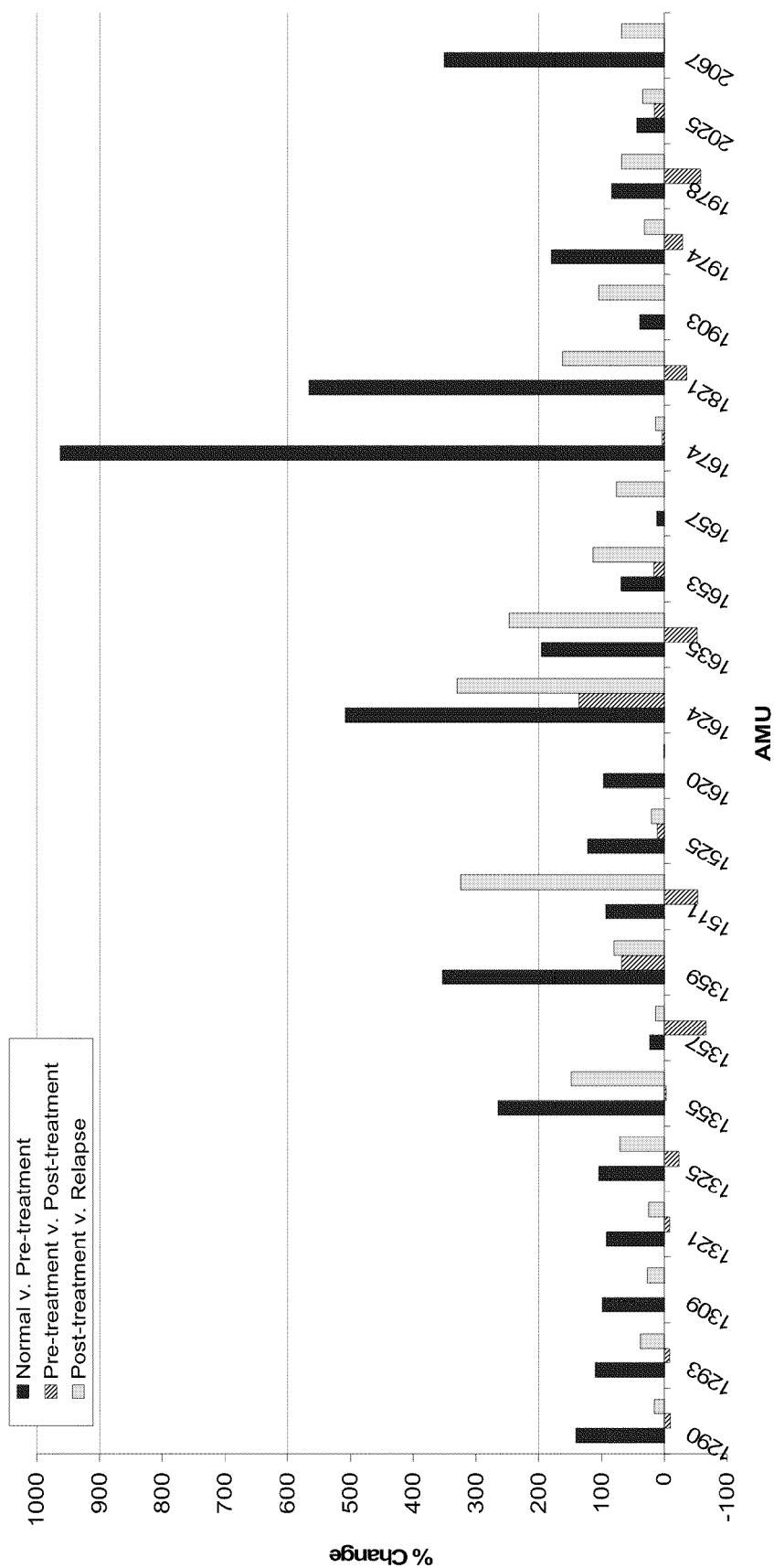
FIG. 4 (peptide masses 1290 m/z to 2067 m/z) is another graph illustrating how a peptide of specific mass and structure increased with lymphoma (Pre-treatment), decreased after a chemotherapy treatment (Post-treatment, remission), and increased with recurrence of lymphoma (Relapse).

When comparing normal serum to serum from the pre-chemotherapy treatment sample in case No. 1, a total of 107 fucosylated peptides changed greater than 50%. Of these 107 peptides, 84 fucosylated peptides were increased in the pre-chemotherapy sample. Only 23 peptides decreased in concentration when compared to the normal dog serum. In the pre-chemotherapy versus post-chemotherapy (post-treatment; remission) samples, 21 peptides increased and 32 decreased post-chemotherapy while the dog was clinically in remission. Subsequent comparison of the post-chemotherapy (post-treatment; remission) serum with serum taken during relapse of lymphoma in case No. 1 revealed 65 fucosylated peptides that changed greater than 50%. Among these peptides, 48 fucosylated peptides increased during relapse of the lymphoma. Fucosylated peptides with the same MS and MS/MS spectrum (i.e., the same fucosylated peptides) were compiled from all three treatment groups (pre-chemotherapy, post-chemotherapy (post-treatment, remission), and relapse (also post-chemotherapy) in the serum from this dog). There were 46 peptides that were similar across all treatment groups which increased with lymphoma then decreased after chemotherapy treatment when the dog was in remission from the cancer. The same 46 fucosylated peptides increased again upon recurrence of the cancer. These peptide masses, graphed as percent change of the N-acetoxy-$d_3$-succinimide ($d_3$) GIST labeled peptide versus the N-acetoxy-$d_0$-succinimide ($d_0$) GIST labeled peptide, are depicted in FIGS. 3 and 4.

Changes in fucosylated peptides were also quantitated comparing normal serum vs. pre-chemotherapy serum in cases No. 2 and 3. In case No. 2, there were 21 fucosylated peptides that changed greater than 50%. Of these 21, 15 increased with lymphoma. A similar trend was observed in case No. 3 in which there were 66 out of 77 fucosylated peptides that increased with lymphoma.

Figure 5:
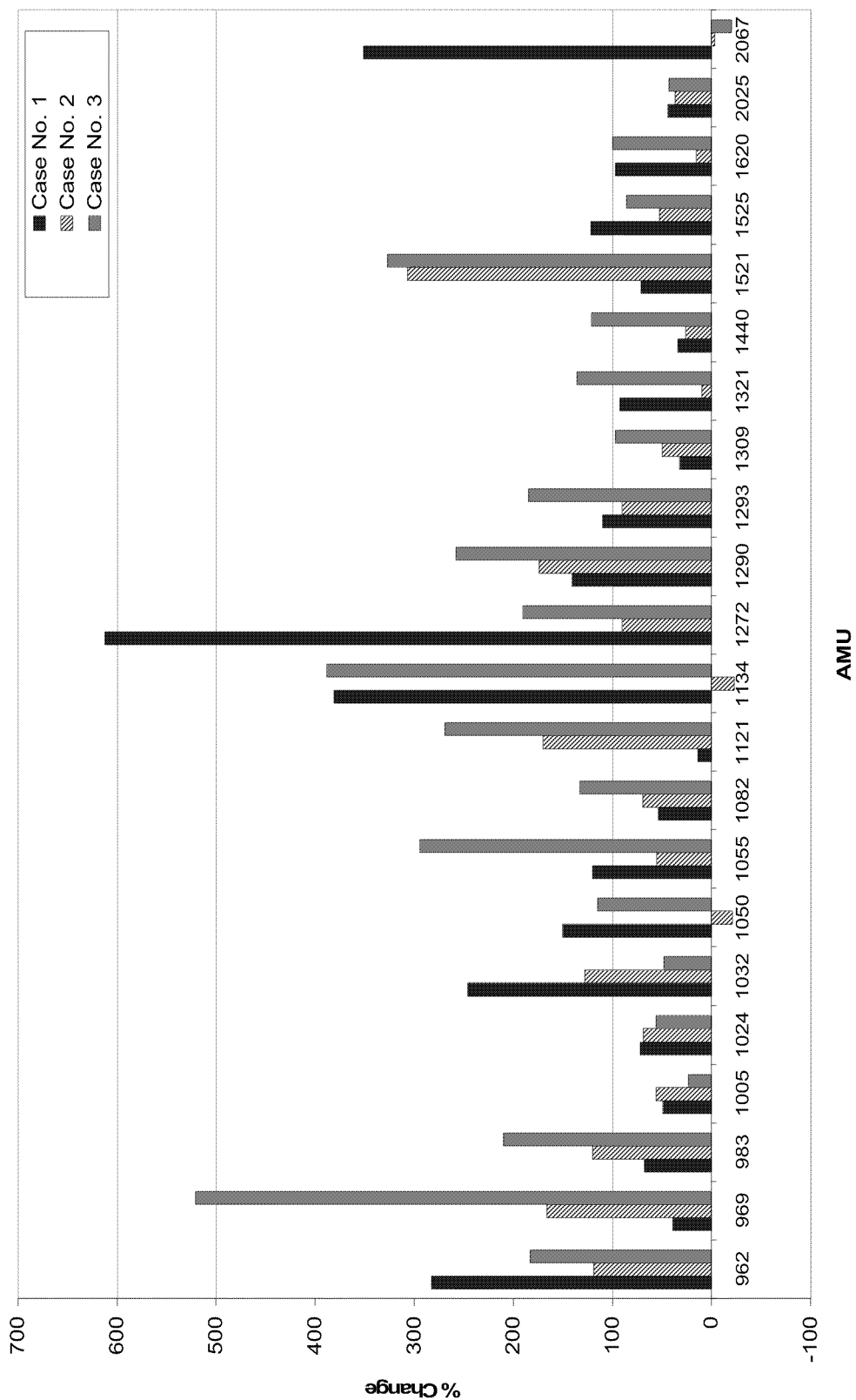
FIG. 5 is a graph illustrating peptides similar in all three subjects (dogs) with respect to the peptide mass profile generated from case No. 1 (Normal vs. Pre-treatment).
Figure 6:
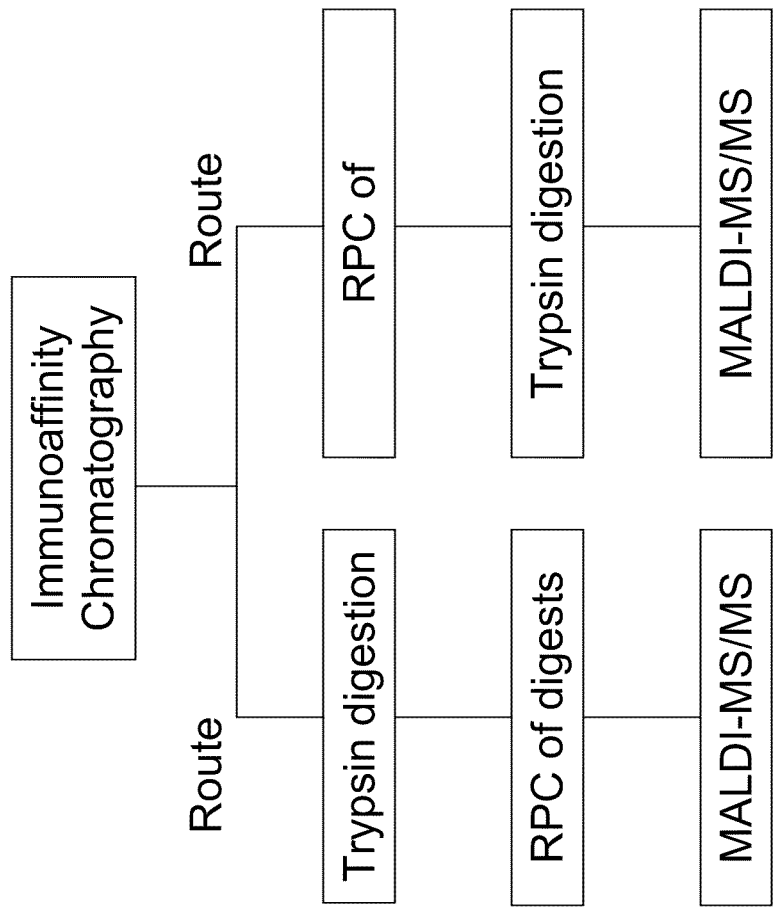
FIG. 6 illustrates one embodiment of the protocols used in the isolation, identification, and quantitative comparison of glycoproteins in human plasma samples.

The proteomic spectra generated by all MALDI-TOF analyses from the three cases were compared and compiled generating a peptide mass profile. FIGS. 3 and 4 are graphs illustrating how peptide masses increased with lymphoma (pre-treatment), decreased post-chemotherapy treatment (post-treatment; remission), and increased with recurrence of lymphoma (relapse). The relative changes in the amount of peptides with masses 754 to 1272 are shown in FIG. 4, and the relative changes in the amount of peptides with peptide masses 1290 to 2067 are shown in FIG. 5. AMU, atomic mass unit. Common to all three dogs, there were 22 peptide masses similar in the normal versus pre-chemotherapy treatment samples. Of these 22 peptide masses, 19 were increased in the serum of all dogs with lymphoma when compared to normal canine serum (FIG. 6).

When comparing lectin affinity selected, fucosylated peptides in normal canine serum versus the pre-treatment serum samples from these dogs, a group of peptides was shown to change. Of those labeled, fucosylated peptides from each dog that changed, greater than 70% were increased in the lymphoma serum samples compared to normal canine serum. Using a similar experimental protocol, increases in serum peptides were previously reported in another dog with lymphoma (Xiong et al., 2003, *J. Proteome Res.* 2: 618-625). While there are no other reports in the literature regarding protein fucosylation and canine lymphoma, increased fucosyltransferase activity and changes in fucosylated glycopeptides have been documented in leukemic B-cell lines and non-Hodgkin's lymphoma. In these reports, plasma fucosyltransferases have been shown to be elevated in human leukemic B-cell lines (Rossowski and Srivastava, 1993, *Eur. J. Cancer and Clin. Onc.* 19: 1431-1437) and in plasma from patients with non-Hodgkin's lymphoma (Khilanani et al., 1978, *Cancer* 41: 701-705). Additionally, biosynthesis of fucosylated peptides in acute-leukemic lymphoblasts has been observed to be an inherent characteristic of that malignant cell type (Rupar and Cook, 1982, *Biochem. J.* 201: 377-385). In this experiment, the elevated levels of fucosylated peptides are likely related to the presence of lymphoma, but are not necessarily all from the neoplastic lymphoma cells.

*Lotus tetragonolobus* lectin selects for α-L-fucosyl residues (Oda et al., 2003, *J. Biol. Chem.* 278: 32439-32447). Since some inflammatory proteins are also known to be fucosylated (Becker and Lowe, 2003, *Glycobiology* 13: 41R-53R), a few of the peptides observed could be due to host response to the cancer. Additionally, some of the changes observed could be due to age, breed, and sex differences between the normal (healthy) dogs in the pooled serum and the dogs with cancer. However, since all of the pre-treatment serum samples from lymphoma cases were compared to a mixed pool of serum from normal male dogs, this would tend to cancel out some breed, age and sex differences. In addition, since the group of fucosylated peptides which changed in dogs with lymphoma were the same in all three dogs, even though they were of different age, sex and breed, this also supports that all of the peptides are related to the presence of the lymphoma itself and/or the physiological responses of the dogs to the lymphoma.

In case No. 1, post-chemotherapy (remission) and relapse serum samples were also obtained. Since the pre-chemotherapy treatment, post-chemotherapy (remission), and relapse samples in this case were taken from the same dog, any changes in fucosylated peptides due to age, breed, sex, or genetic variation were eliminated. Although the majority of the fucosylated peptides observed when comparing the pre-chemotherapy versus post-chemotherapy (remission) sample decreased; a few increased after chemotherapy. Those peptides that decreased can be indicators that the dog responded to treatment and that the cancer was in remission. Those peptides that increased post-chemotherapy can be due in part to the side effects of the chemotherapeutic protocol, as these agents can induce changes in the concentrations of inflammatory serum proteins due to their inherent toxicity (Lucas et al., 2004, *J. Amer. Anim. Hosp. Assoc.* 40: 292-299).

Increases in fucosylation of serum/plasma proteins have been reported in human lymphoma. Non-Hodgkin's lymphoma patients who did not respond to chemotherapy treatment had elevated plasma fucosyltransferases, leading to enhanced fucosylation. These enzyme levels returned to normal during remission (Rossowski and Srivastava, 1993, *Eur. J. Cancer and Clin. Onc.* 19: 1431-1437). Hence, in the case of dog No. 1, an increase in fucosylated peptides pre-chemotherapy and a subsequent decrease in fucosylated peptides post-chemotherapy is consistent with that study. When the post-chemotherapy sample (clinical remission) was compared to the sample taken when the dog relapsed with the lymphoma, the majority of the same fucosylated peptides increased with relapse.

Mass spectrometry (MS) was used for proteolytic peptide fingerprinting in order to generate a peptide mass profile. Typically, amino acid sequencing by MS/MS peptide fragmentation is used to query theoretical mass spectral data in sequence databases, permitting protein identification. Unfortunately, the canine genome was sequenced relatively recently and therefore, the canine proteins in sequence databases are incomplete. This has hindered progress in accurately identifying the proteins from which the altered serum peptides originated in these lymphoma cases. However, as canine protein sequences become available, it should be possible to identify the individual proteins.

EXAMPLE 2

Use of Glycan-Targeting Antibodies to Identify Cancer-Associated Glycoproteins in Plasma of Breast Cancer Patients This is an example of using immunoaffinity chromatography (IAC) to isolate and identify potential cancer biomarker glycoproteins by targeting disease associated glycans. Glycoproteins were selected from plasma of disease free and breast cancer patients with an anti-Lewis x (Le$^x$) IAC column. After extensive washing of the IAC column to remove abundant proteins, the selected proteins were eluted with an acidic mobile phase and identified in two ways. The protocol used in Route A involved the steps of tryptic digestion, reversed phase chromatographic fractionation of the digest, and identification of peptides in collected RPC fractions by MALDI-MS/MS. Route B differed in that IAC selected proteins were further fractionated by reversed phase chromatography (RPC) before proteolysis of individual chromatographic fractions and identification by MALDI-MS/MS. Route A was the more efficacious of the two protocols in total number of proteins identified. Of the 26 proteins identified, 9 were found to be potential breast cancer marker candidates based on their elevation in breast cancer patients.

Materials and Chemicals.

Agarose-conjugated anti-Lewis×IgM was purchased from Santa Cruz Biotech (Santa Cruz, Calif.). iTRAQ™ and the ABI 4700 Proteomics Analyzer Calibration Mixture (4700 Cal Mix, bradykinin, angiotensin I, glu$^1$-fibrinopeptide B, ACTH fragment 1-17, ACTH fragment 18'-39, and ACTH fragment 7-38) were purchased from Applied Biosystems (ABI, Foster City, Calif.). Normal pooled human plasma was generously supplied by the National Institute of Standards and Technology (NIST, Gaithersburg, Md.). Human breast cancer plasma from ductal carcinoma patients was purchased from Asterand, Inc. (Detroit, Mich.). Potassium phosphate monobasic, acetic acid, trifluoroacetic acid (TFA), and HPLC grade acetonitrile were purchased from Mallinckrodt Chemicals (Phillipsburg, N.J.). Glycine, α-Cyano-4-hydroxy-cinnamic acid (CHCA), proteomics grade N-p-tosyl-phenylalanine chloromethyl ketone (TPCK)-treated trypsin, 4-(2-hydroxyethyl)-1-piperazine ethanesulfonic acid (HEPES), iodoacetic acid (IAA), and L-cysteine were obtained from Sigma-Aldrich (St. Louis, Mo.). Sodium dodecyl sulfate (SDS) was purchased from Fluka Biochemika (Buchs, Switzerland). Dithiothreitol (DTT) and urea were provided by Bio-Rad Laboratories (Hercules, Calif.). The DI water system and $C_{18}$ ZipTips were purchased from Millipore (Boston, Mass.).

Immunoaffinity Chromatography (IAC).

Agarose-conjugated anti-Lewis×antibody was self-packed in a 4.6×50 mm column. Protein concentration of human plasma from the NIST and ductal carcinoma patients was estimated using Bradford assay. This information was used to ensure that the total amount of protein injected on the IAC column was the same with each sample. Human plasma was applied directly to this soft-gel immunosorbent column with mobile phase A (0.15 M phosphate buffered saline, pH 7.4) at a flow rate of 0.3 mL/min. Following extensive washing with mobile phase A, the IAC column was eluted with buffer B (0.1 M glycine/2% acetic acid-HCl buffer, pH 2.5). Elution curves were obtained with an absorbance detector operating at 280 nm using a ProteomeLab™ PF 2D liquid chromatograph from Beckman Coulter, Inc. (Fullerton, Calif.).

Reversed Phase Chromatography of Selected Proteins.

Chromatographic fractionation of proteins was achieved with the ProteomeLab™ PF 2D. Affinity-selected proteins from the first separation dimension were fractionated in the second dimension using a 4.6×50 mm non-porous particles C-18 RPC column (Beckman Coulter, Inc.). Proteins were eluted from the RPC column with either a 45 or 90 min linear gradient ranging from pure solvent A (DI water with 0.1% TFA) to 70% solvent B (acetonitrile with 0.09% TFA). Protein elution was monitored at 214 nm.

Mass Spectrometry Based Protein Identification.

Glycoproteins carrying the Le$^x$ antigen were identified with a 4800 Proteomics Analyzer mass spectrometer (ABI). Individual peaks were collected from the antibody column or the RPC column and following trypsin digestion, proteins were identified based on the presence of peptide fragments identified from tandem mass spectra.

A Pepmap C18 trap column and a nano-column (Zorbax 300sB-C18, 3.5 µm, 100 µm i.d., 15 cm length, Agilent Technologies, Santa Clara, Calif.) were used with an Agilent 1100 Series HPLC (Agilent Technologies) for desalting and reversed-phase chromatography (RPC) of peptides derived from tryptic digestion of affinity-selected proteins, respectively. The RPC separation was achieved using a 40 min linear gradient from 98% solvent A:2% solvent B to 60% solvent A:40% solvent B at a flow rate of 800 nL/min. Solvent A was composed of DI water to which trifluoroacetic acid (TFA) had been added to a concentration of 0.1%. Solvent B was prepared with acetonitrile (ACN) to which TFA had been added to a concentration of 0.1%. Peptides were collected directly from the RPC column onto a stainless steel MALDI target utilizing a micro-fraction collector and MALDI spotter driven by an Agilent 1100 LC System. Column eluent was combined in a mixing tee with MALDI matrix (α-cyano-4-hydroxycinnamic acid, 8 mg/mL in 60% ACN/0.1% TFA) delivered at 1.2 µL/min. Peptides were analyzed with an ABI 4800 Proteomics Analyzer mass spectrometer in the positive ion mode. The 4800 Proteomics Analyzer was equipped with TOF/TOF ion optics and a 200 Hz Nd:Yag laser. Automated acquisition of MS and MS/MS data was controlled by 4000 Explorer software. Automated MS/MS data analysis was performed utilizing Protein Pilot software 2.0 using the Pro Group™ algorithm (ABI) for protein identification. The minimum acceptance criterion for peptide identification was the 99% confidence level. Proteins were identified based on the presence of at least two peptides from a protein identified by the Pro Group™ algorithm at the 99% confidence level. An unused score cutoff of 4 was the minimum value for identifying proteins with the Protein Pilot 2.0 software. Proteins are listed in Tables according to their Swiss-Prot entry names and accession numbers.

Quantitative Comparison of Protein Abundance with iTRAQ.

Tryptic digested proteins from either IAC fractions, size exclusion chromatography (SEC) or RPC fractions were labeled with iTRAQ™ reagent to compare the control plasma and cancer patient plasma samples. Trypsin digestion and labeling with iTRAQ™ reagent were performed according to the supplier's guidelines (ABI). The NIST control sample was labeled with the 114-dalton iTRAQ labeling agent while cancer samples were labeled with the 115-dalton iTRAQ labeling agent. The 116-dalton and 117-dalton iTRAQ reagents were also used in cancer patient analyses.

Again the Pepmap C18 trap column and a nano-RPC column were used for desalting and RPC of peptides from affinity-selected proteins as described above in the mass spectrometry based protein identification section. Peptides were analyzed on the ABI 4800 Proteomics Analyzer mass spectrometer. Automated acquisition of MS and MS/MS data was controlled by 4000 Series Explorer software. Automated MS/MS data analysis was performed utilizing Protein Pilot software 2.0 with the Pro Group™ algorithm for protein identification and quantification of iTRAQ reporter ions. Only peptides that were completely labeled with iTRAQ reagent at their N-terminus and lysine residues and had a non-zero relative isotope ratio were considered in comparative proteomics measurements.

Analytical Strategy.

Subsequent to IAC of 30-600 µL samples of plasma, the selected glycoproteins were desorbed from affinity columns and identified in one of two different ways (FIG. 6). IAC selected glycoproteins in Route A where subjected to a three step protocol involving trypsin digestion, RPC of the tryptic digested peptides, and identification of peptides in RPC fractions by MALDI-MS/MS. This approach is referred to herein as the "bottom-up" method to preserve similar terminology analogous with the "bottom-up shot-gun" proteomics method (An et al., 2006, *Anal. Chem.* 78: 7110-7120).

Route B (FIG. 6) differed in that all chromatographic fractionation was carried out at the protein level. This approach will be referred to as the "top-down" approach because of its similarity to a method of the same name used in 2-D electrophoresis. The glycoprotein fraction collected from IAC was further fractionated with a non-porous particle RPC (np-RPC) column having an octadecyl silane stationary phase.

Protein peak capacity in the range of 50 was observed with this column. Glycoprotein fractions collected from the np-RPC column were tryptic digested and after Zip-Tip removal of salts were analyzed directly by MALDI-MS/MS. Mass spectral data was analyzed as described in the METHODS.

Differences in the concentration of glycoprotein isoforms between samples were examined using stable isotope coding of samples with the commercial iTRAQ reagent (Matta et al., 2008, *J. Proteome Res. A-J*). Breast cancer patient plasma samples were compared with plasma from controls showing no clinically recognizable symptoms of cancer.

Affinity Chromatography.

IAC columns (4.6×50 mm) with anti-Le$^x$ antibody immobilized on agarose were used in this work. Up to 600 µL of protein concentration matched plasma samples were applied to the column using pH 7.4, 0.15 M phosphate buffered saline (mobile phase A) at a flow rate of 0.3 mL/min. This low flow rate was used to avoid compression of the soft gel sorbent. Following a 15 mL wash with mobile phase A the affinity column was eluted with buffer B (0.1 M glycine/2% acetic acid-HCl buffer, pH 2.5) at the same flow rate. Columns were recycled with sequential 10 column volume washes of mobile phase B and A, respectively. The affinity column was used in processing 30 samples over the course of three months with no apparent deterioration in efficacy.

Figure 7:
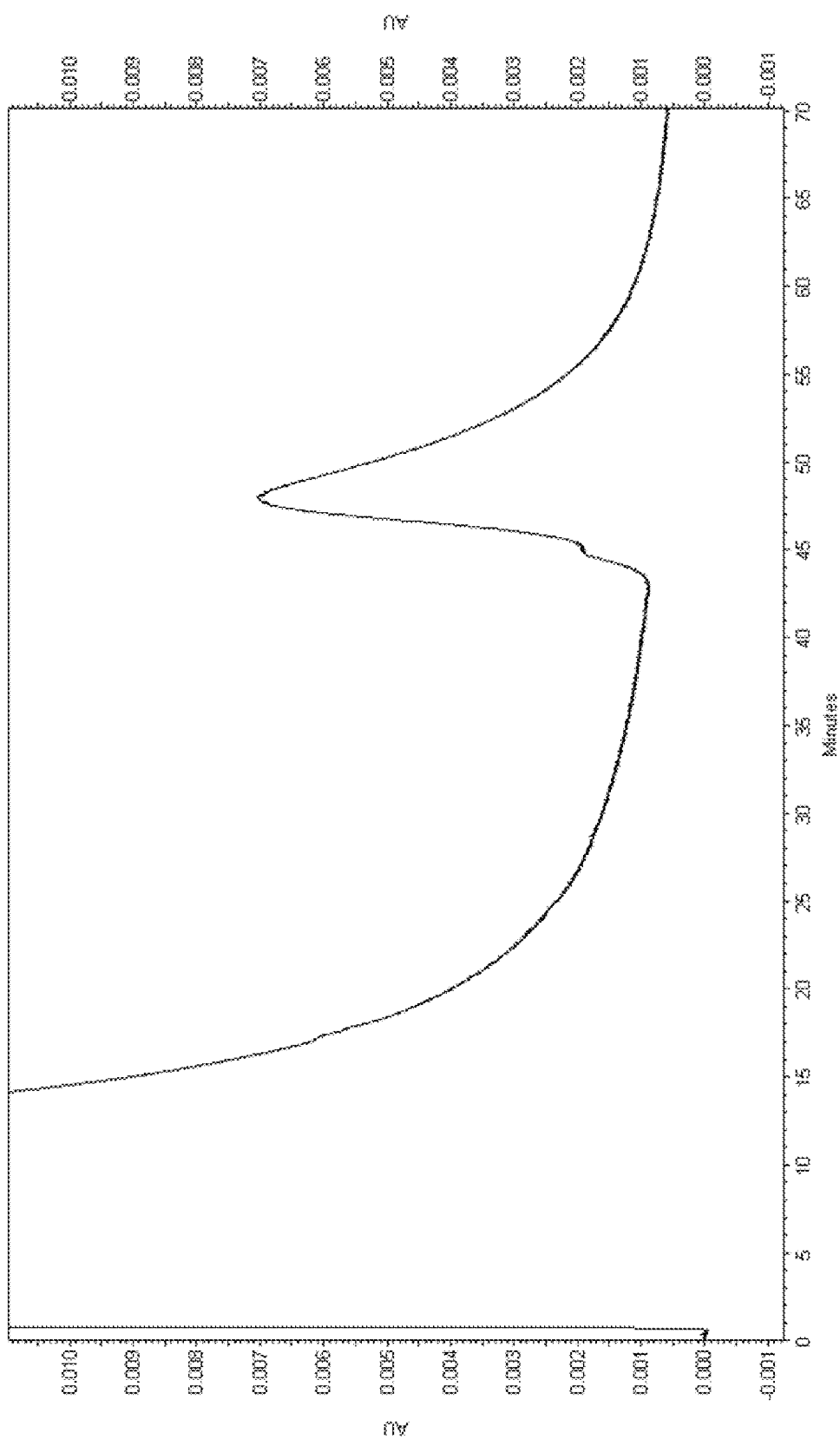
FIG. 7 is a graph showing an immunoaffinity chromatogram of a breast cancer (stage 2) human patient plasma sample.

The presence of albumin and a few other abundant proteins is a major problem in proteomics of plasma. There is concern in any type of chromatography that non-specific binding of these abundant proteins to columns will later mask the identification of low abundance proteins. Fortunately, the magnitude of this problem can be assessed by modeling. The binding constant ($K_B$) of an abundant protein partitioning with the surface of a chromatography sorbent can be described by the equation $$K_B = \frac{[P_{NSB}]}{[S][P]} \quad (1)$$

where [$P_{NSB}$] is the concentration of protein adsorbed on the surface of the chromatography sorbent, [P] is the concentration of the protein in solution above the surface, and [S] is specific sorbent concentration. The binding constant ($K_B$) and the chromatography partition coefficient ($K_D$) of a protein can be related by the chromatographic retention equation below. Retention in liquid chromatography is generally described in terms of a dimensionless capacity factor (k') defined by the equations $$k' = K_D \phi = \frac{[P_{NSB}]}{[P]} \cdot \frac{V_s}{V_m} \quad (2)$$

where ø is the stationary to mobile phase ratio ($V_s/V_m$) in a unit length of column. Substituting equation 1 into 2

$$K_D = \frac{[P_{NSB}]}{[P]} = K_B[S] \quad (3)$$

the relationship between chromatographic retention (k') and $K_B$ in the equation $$k' = K_B[S]\phi \quad (4)$$

shows that the retention of abundant proteins is proportional to both their binding constant and the specific sorbent volume (or surface area) of the chromatographic sorbent. The binding constant for a non-specifically bound protein would seldom be greater than $10^4$ whereas the phase ratio will be 1 or less. Since antibody concentration would not exceed $10^{-3}$ to $10^{-4}$ M, k' would be 10 or less according to equation 4. This means that a 10 column volume wash would elute most of abundant proteins. That is what was seen in FIG. 7, which is a graph showing an immunoaffinity chromatogram of a breast cancer (stage 2) patient plasma sample. A 20 µL sample of plasma was applied directly to a 4.6×50 mm column packed with Agarose to which anti-Lex antibody had been immobilized. The column was eluted initially with 0.15 M phosphate buffered saline, (pH 7.4) at 0.3 mL/min for 35 min then switched to a mobile phase containing 0.1 M glycine/2% acetic acid-HCl (pH 2.5) for an additional 35 min at the same flow rate. Absorbance was monitored at 280 nm. When the column was washed after sample injection with 10-15 column volumes of loading buffer, absorbance from abundant proteins had almost returned to zero. From this it is concluded that abundant proteins do not have to be removed before antibody selection of glycans. This does not mean, however, that abundant proteins will not be seen in antibody selected samples. Abundant proteins could potentially complex with higher binding affinity to proteins selected with antibodies and accompany these binding partners in affinity fractionation.

Although sensitivity is higher when absorbance is monitored at 205-215 nm, absorbance was monitored at 280 nm during elution (FIG. 7) to avoid desorbing agent perturbations of the base line that complicate antigen quantification. Assuming that the bulk of the absorbance in these chromatograms is from protein, it can be roughly estimated that 0.07% of the protein from the chromatogram of the normal patient plasma sample in FIG. 7 carries the Le$^x$ antigen. Using this method the relative amount of Le$^x$ bearing protein was determined in the plasma of a series of cancer patients. Table 3 below shows the relative amount of glycoprotein from human plasma samples selected with an anti-Le$^x$ IAC column. The NIST sample was a normal control whereas all the cancer samples came from breast cancer patients with ductal carcinomas. In all cases the amount of Le$^x$ antigen in cancer patient samples was at least double that of the normal control. Quantification of total antigen bearing proteins with this chromatographic approach is easier and faster than immunological assay methods normally used to estimate Lewis antigens. A second advantage of IAC is that with large sample volumes, low abundance antigens can be enriched.

TABLE 3

Relative amount of glycoprotein from human plasma samples selected with an anti-Le$^x$ IAC column

| Sample | Binding percent (%) | Ratio |
|---|---|---|
| NIST | 0.066 | 1.0 |
| stage2a-1 | 0.127 | 1.8 |
| stage2a-2 | 0.190 | 2.9 |
| stage4-1 | 0.100 | 1.5 |
| stage4-2 | 0.187 | 2.8 |

Reversed Phase Chromatography of IAC Selected Proteins.

Chromatographic fractionation of glycoproteins is generally carried out at near physiological pH to maintain native structure. The decision to fractionate the glycoproteins selected with the IAC columns by RPC in this work was based on the fact that they were eluted in IAC with very acidic mobile phase and had probably undergone some degree of denaturation. Moreover, it was thought they might not recover their structure when returned to physiological pH. Partially or totally denatured proteins do not chromatograph well in almost all modes of chromatography except RPC. In contrast to other chromatographic modes used in protein fractionation, RPC separations are best at acidic pH. Mobile phases used in the elution of IAC and RPC columns are therefore very compatible. In fact, proteins can be directly transferred from an IAC column to an RPC column where they refocus at the inlet of the second column (Janis and Regnier, 1989, *Anal. Chem.* 61: 1901-1906). This is a great advantage when the elution volume from the affinity column is large.

Figure 8:
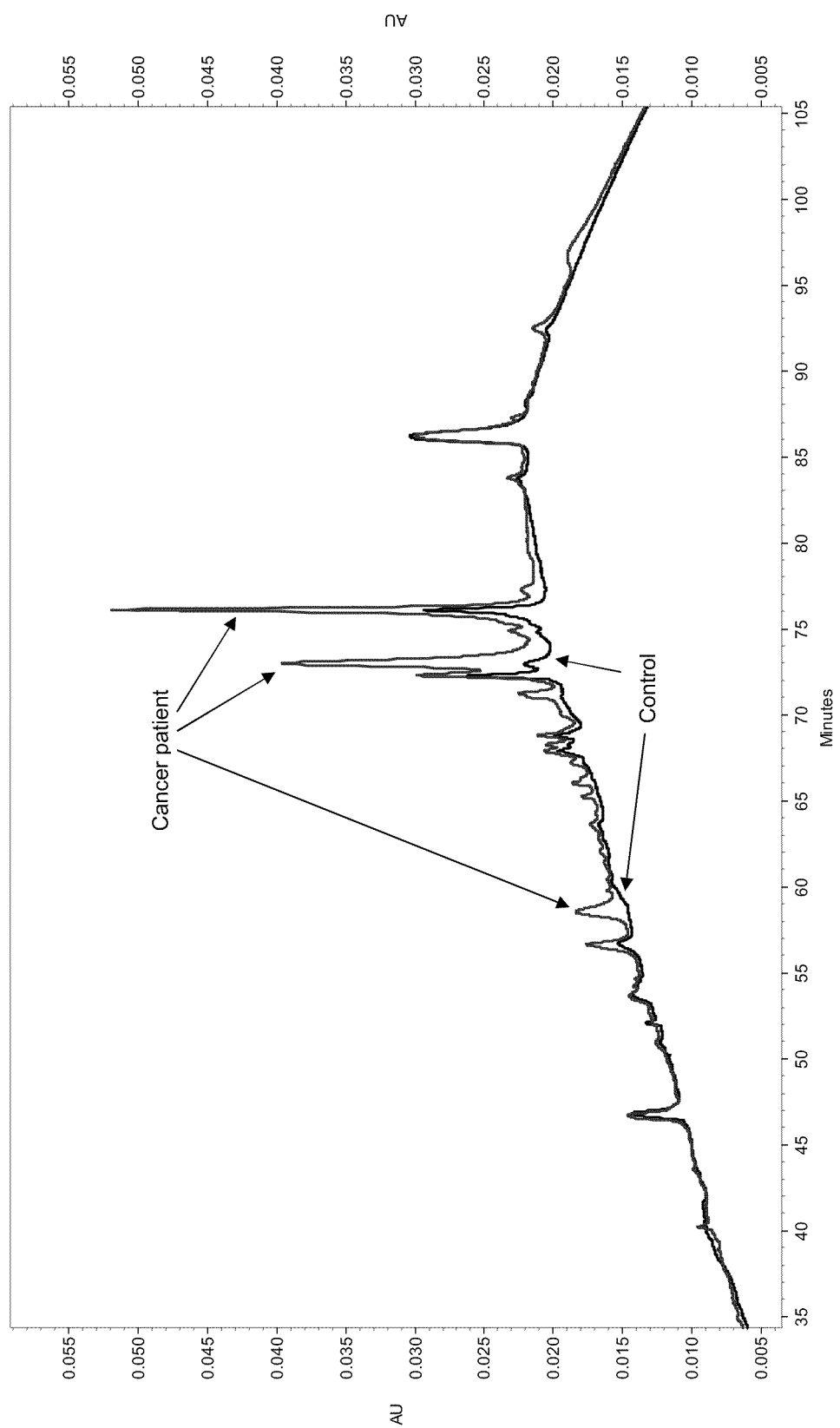
FIG. 8 is a graph showing RPC (reversed phase chromatography) chromatograms of the protein fraction selected from human plasma by an anti-Le$^x$ antibody immunoaffinity chromatography (IAC) column.

FIG. 8 shows high resolution RPC chromatograms of the protein fraction selected from human plasma by an anti-Le$^X$ antibody IAC column. Data from a NIST pooled plasma control and from a stage 4 breast cancer patient are shown. All substances eluting beyond 80 minutes were not peptides based on mass spectral analysis. Based on the complexity of the human blood proteome, this RPC chromatogram shows that IAC provides a very substantial simplification of plasma in a single step. Moreover, there are clear quantitative differences between the cancer patient and normal-control chromatograms (FIG. 8). The limit of detection for a single protein peak was roughly 1 ng with the 4.6×50 mm RPC column. Going to a 100 μm ID micro bore column the detection limit could potentially drop more than $10^3$.

Protein Identification.

Proteins selected by the IAC column were identified in two ways (FIG. 6). In Route A, IAC selected proteins were trypsin digested and cleavage fragments fractionated (FIG. 4) on a C-18 capillary RPC column. Fractions collected from the RPC column were spotted on a MALDI plate and identified by MALDI-MS/MS. Proteins identified by this protocol are shown in Table 4, which is a list of anti-Le$^x$ selected plasma proteins identified by tandem mass spectrometry of their tryptic peptides.

A more detailed presentation of the MS/MS data can be found in Table 6. A total of 26 glycoproteins were identified in this approach based on the identification of two or more peptides from a protein at a confidence level of 99%. This is roughly the number of chromatographic peaks seen in FIG. 7. Most of the mass spectral identifications were based on 4-10 peptides, representing 15-50% sequence coverage of the primary structure. More proteins were found in stage-2 and stage-4 cancer patient samples than the NIST pooled control. It is important to note that although abundant proteins were not removed from samples, they caused no problem in glycoprotein identification. In fact, they were generally not seen at all in untreated plasma samples.

Protein identification in Route B was achieved by collecting protein fractions during the RPC separation as in FIG. 8, followed by trypsin digestion of the proteins in the collected fractions, and after desalting and concentrating samples with Zip-Tips, peptides were identified by direct MALDI-MS/MS analysis. Proteins identified by this procedure are found in Table 4. A more detailed presentation of the MS/MS data can be found in Table 6.

TABLE 4

Anti-Le$^x$ selected plasma proteins identified by tandem mass spectrometry of their tryptic peptides

| N | % Cov. | Swiss-Prot Accession # and entry name | Name | Rt. A | Rt. B |
|---|---|---|---|---|---|
| 1 | 22.4 | P02649\|APOE_HUMAN | Apolipoprotein E (Apo-E) | + | + |
| 2 | 32.5 | P10909\|CLUS_HUMAN | Clusterin | + | + |
| 3 | 12.0 | P00748\|FA12_HUMAN | Coagulation factor XII | + | |
| 4 | 16.3 | P02747\|C1QC_HUMAN | Complement C1q subcomponent subunit C | + | |
| 5 | 15.8 | P04264\|K2C1_HUMAN | keratin 1 | + | + |
| 6 | 19.2 | P13645\|K1C10_HUMAN | keratin 10 | + | + |
| 7 | 19.2 | P02671\|FIBA_HUMAN | Fibrinogen alpha chain | + | + |
| 8 | 20.8 | P02675\|FIBB_HUMAN | Fibrinogen beta chain | + | + |
| 9 | 11.5 | P02679\|FIBG_HUMAN | Fibrinogen gamma chain | + | + |
| 10 | 5.7 | P02751\|FINC_HUMAN | Fibronectin | + | |
| 11 | 18.5 | Q08380\|LG3BP_HUMAN | Galectin-3-binding protein | + | |
| 12 | 15.0 | P01877\|IGHA2_HUMAN | Ig alpha-2 chain C | + | + |
| 13 | 35.3 | P01859\|IGHG2_HUMAN | Ig gamma-2 chain C | + | + |
| 14 | 31.7 | P01860\|IGHG3_HUMAN | Ig gamma-3 chain C | + | |
| 15 | 23.5 | P01777\|HV316_HUMAN | Ig heavy chain V-III region TEI | + | |
| 16 | 80.2 | P01834\|KAC_HUMAN | Ig kappa chain C region | + | |
| 17 | 43.0 | P01871\|MUC_HUMAN | Ig mu chain C region | + | + |
| 18 | 11.6 | P35908\|K22E_HUMAN | Keratin, type II cytoskeletal 2 epidermal | + | + |
| 19 | 5.9 | P01042\|KNG1_HUMAN | Kininogen-1 | + | |
| 20 | 15.2 | P00747\|PLMN_HUMAN | Plasminogen | + | |
| 21 | 43.6 | P02776\|PLF4_HUMAN | Platelet factor 4 | + | |
| 22 | 22.1 | P10720\|PF4V_HUMAN | Platelet factor 4 variant | + | |
| 23 | 4.1 | Q92954\|PRG4_HUMAN | Proteoglycan-4 | + | |
| 24 | 59.0 | P02735\|SAA_HUMAN | Serum amyloid A protein | + | |
| 25 | 23.4 | P04004\|VTNC_HUMAN | Vitronectin | + | |
| 26 | 2.6 | P35527\|K1C9_HUMAN | Keratin, type I cytoskeletal 9 | | + |

Quantification of Protein Concentration Differences.

The disease marker premise is that there will be quantitative and perhaps even qualitative variations in one or a pattern of substances in association with the progression of a disease (Linkov et al., 2007, *Expert Opin. Med. Diagn.* 1: 129-136). The issue with the 26 affinity selected glycoproteins described herein is which, if any have the potential to be breast cancer biomarkers. This question is most easily addressed with a method that allows disease free and cancer patient plasma samples to be compared in vitro.

Comparative analyses of plasma proteins from human subjects have been achieved with an accuracy ±4-6% relative standard deviation (Qiu and Regnier, 2005, *Anal. Chem.* 77: 2802-2809) by differential isotope coding of tryptic digests according to sample origin. Because trypsin digestion produces an amino group on all peptides in a digest except a very small number at blocked N-termini, an isotope coding agent that reacts with primary amines was used to globally derivatize all peptides in a proteolytic digest (Regnier and Julka, 2006, *Proteomics* 6: 3968-3979).

Comparative quantification studies were carried out using the strategy outlined in Route A of FIG. 6 to compare two samples at a time that had been differentially coded with the iTRAQ stable isotope tags. These tags are N-hydroxysuccinimide (NHS) esters of N-methyl piperazines that react with primary amines on peptides. They are prepared in such a way as to produce either four or eight isobaric coding reagents that allow multiplexing of 4 or 8 samples simultaneously (Ross et al., 2004, *Mol. Cell. Proteomics* 3: 1154-1169). Although capable of examining 4-8 samples at a time, only two were examined concurrently in these studies. Generally the two lightest iTRAQ reagents were used. Cleavage at the carbonyl group of the piperazine ring produced reporter ions at 114.1 and 115.1 amu, at unit mass differences. Changes in protein concentration were identified from the difference in monoisotopic peak areas of the reporter ions. The piperazine ring appears to minimize ions generated from less informative fragmentation pathways, thereby facilitating the representation of "b" and "y" ions.

iTRAQ labeling was carried out after: 1) IAC selection of glycoproteins from a sample; and 2) tryptic digestion of the affinity selected fraction using the protocol developed by the reagent supplier. Data from the comparison of a stage-2 breast cancer patient sample with the NIST control is seen in Table 5, which shows a list of proteins of elevated concentration in a stage-2 cancer patient relative to the pooled NIST control. Nine of the 26 proteins in Table 4 are elevated in this cancer patient. Although these 9 proteins were found to be elevated in 6 other stage-2 and stage-4 patients as well, that data is not presented. It was thus discovered that in vivo stable isotope coding clearly allows comparison of samples to be made during the course of mass spectral identification of proteins. The nine proteins listed in Table 5 (SEQ ID NO:1-SEQ ID NO:9) are thus considered to be breast cancer biomarker glycoproteins.

TABLE 5

Proteins of elevated concentration in a stage-2 cancer patient relative to the pooled NIST control

| N | Swiss-Prot Accession # and entry name | SEQ ID NO | Protein name | Ratio: Stage-2/NIST* |
|---|---|---|---|---|
| 1 | P10909\|CLUS_HUMAN | 1 | Clusterin | 9 |
| 2 | P02671\|FIBA_HUMAN | 2 | Fibrinogen alpha chain | 8 |
| 3 | P02675\|FIBB_HUMAN | 3 | Fibrinogen beta chain | 12 |
| 4 | P01871\|MUC_HUMAN | 4 | Ig mu chain C region | 27 |
| 5 | P01042\|KNG1_HUMAN | 5 | Kininogen-1 | 7 |
| 6 | P02776\|PLF4_HUMAN | 6 | Platelet factor 4 | 15 |
| 7 | P10720\|PF4V_HUMAN | 7 | Platelet factor 4 variant | 7 |
| 8 | P02735\|SAA_HUMAN | 8 | Serum amyloid A protein | 11 |
| 9 | P04004\|VTNC_HUMAN | 9 | Vitronectin | 5 |

*Values were rounded to the nearest whole number.

Table 6 is a list of anti-Le$^x$ selected proteins identified from plasma samples.

TABLE 6

Anti-Le$^x$ selected protein identifications from plasma samples

| N | % Cov. | Swiss-Prot Accession # and entry name | Name | Rt. A | Rt. B | IAC proof #of identified peptides per protein with peptide confidence levels | RPC proof # of identified peptides per protein with peptide confidence levels |
|---|---|---|---|---|---|---|---|
| 1 | 22.4 | P02649\|APOE_HUMAN | Apolipoprotein E precursor (Apo-E) | + | + | 4 peptides with 99% confidence | good MS match with theoretical MS, one peptide of 99% confidence |
| 2 | 32.5 | P10909\|CLUS_HUMAN | Clusterin | + | + | 6 peptides with 99% confidence & 1 peptide with 90% confidence | 9 peptides with 99% and 3 peptides with 93%, 93%, 92% confidence levels in RPC |
| 3 | 12.0 | P00748\|FA12_HUMAN | Coagulation factor XII | + | | 4 peptides with 99% confidence | |
| 4 | 16.3 | P02747\|C1QC_HUMAN | Complement C1q subcomponent subunit C | + | | 2 peptides with 99% confidence | |
| 5 | 15.8 | P04264\|K2C1_HUMAN | keratin 1 | + | + | 8 peptides with 99% confidence | identified multiple times with two peptide with 99% confidence in RPC |
| 6 | 19.2 | P13645\|K1C10_HUMAN | keratin 10 | + | + | 6 peptides with 99% confidence & 1 peptide with 90% confidence | |
| 7 | 19.1 | P02671\|FIBA_HUMAN | Fibrinogen alpha chain | + | + | 6 peptides with 99% confidence & 1 peptide with 90% confidence | |
| 8 | 20.8 | P02675\|FIBB_HUMAN | Fibrinogen beta chain | + | + | 6 peptides with 99% confidence | 2 peptides with 99% confidence |

TABLE 6-continued

Anti-Le$^x$ selected protein identifications from plasma samples

| N | % Cov. | Swiss-Prot Accession # and entry name | Name | Rt. A | Rt. B | IAC proof # of identified peptides per protein with peptide confidence levels | RPC proof # of identified peptides per protein with peptide confidence levels |
|---|---|---|---|---|---|---|---|
| 9 | 11.5 | P02679\|FIBG_HUMAN | Fibrinogen gamma chain | + | + | 3 peptides with 99% confidence | 2 peptides with 99%, 96% confidence |
| 10 | 5.7 | P02751\|FINC_HUMAN | Fibronectin | + |   | 3 peptides with 99% confidence |   |
| 11 | 18.5 | Q08380\|LG3BP_HUMAN | Galectin-3-binding protein | + |   | 5 peptides with 99% confidence |   |
| 12 | 15.0 | P01877\|IGHA2 HUMAN | Ig alpha-2 chain C region | + | + | 4 peptides with 99% confidence | 1 peptide with 96% confidence. |
| 13 | 35.3 | P01859\|IGHG2 HUMAN | Ig gamma-2 chain C region | + | + | 5 peptides with 99% confidence & 1 peptide with 90% confidence | 2 peptides with 99%, 96% confidence |
| 14 | 31.7 | P01860\|IGHG3_HUMAN | Ig gamma-3 chain C region | + |   | 4 peptides with 99% confidence & 1 peptide with 92% confidence |   |
| 15 | 23.5 | P01777\|HV316_HUMAN | Ig heavy chain V-III region TEI | + |   | 2 peptides with 99% confidence |   |
| 16 | 80.2 | P01834\|KAC_HUMAN | Ig kappa chain C region | + |   | 5 peptides with 99% confidence |   |
| 17 | 42.9 | P01871\|MUC_HUMAN | Ig mu chain C region | + | + | 9 peptides with 99% confidence | 3 peptides with two 99%, & one 71% confidence level |
| 18 | 11.6 | P35908\|K22E_HUMAN | Keratin, type II cytoskeletal 2 epidermal | + | + | 2 peptides with 99% confidence | 2 peptides with 99% & 97% confidence, also identified twice with good MS match with theoretical MS with 1 peptide having 99% confidence |
| 19 | 5.9 | P01042\|KNG1_HUMAN | Kininogen-1 precursor | + |   | 2 peptides with 99% confidence |   |
| 20 | 15.2 | P00747\|PLMN_HUMAN | Plasminogen precursor | + |   | 2 peptides with 99% confidence |   |
| 21 | 43.6 | P02776\|PLF4_HUMAN | Platelet factor 4 precursor | + |   | 4 peptides with 99% confidence |   |
| 22 | 22.1 | P10720\|PF4V_HUMAN | Platelet factor 4 variant precursor | + |   | 2 peptides with 99% confidence |   |
| 23 | 4.1 | Q92954\|PRG4_HUMAN | Proteoglycan-4 precursor | + |   | 3 peptides with 99% confidence |   |
| 24 | 59.0 | P02735\|SAA_HUMAN | Serum amyloid A protein precursor | + |   | 2 peptides with 99% confidence & 1 peptide with 90% confidence |   |
| 25 | 23.4 | P04004\|VTNC_HUMAN | Vitronectin precursor | + |   | 7 peptides with 99% confidence & 1 peptide with 90% confidence |   |
| 26 | 2.6 | P35527\|K1C9_HUMAN | Keratin, type I, cytoskeletal 9 |   | + |   | 1 peptide was identified 3 times with 99% confidence. |

Antibodies targeting peptide epitopes in proteins are seldom used in discovery proteomics because 1) they are too specific and 2) known protein immunogens are required for antibody production. Protein immunogens are seldom available for antibody production in the discovery phase. But even if they were, these antibodies capture a single protein, or at most several proteins of closely related primary structure. This makes it difficult to conduct a broad, antibody based search for disease associated proteins. In contrast, glycan-targeting antibodies are more general. The same glycan is generally appended to multiple proteins and as a consequence a single antibody targeting this glycan will capture and enrich many proteins from a complex mixture. Enrichment and quantification of the 26 proteins captured by a single glycan-targeting antibody described herein would have required 26 protein directed antibodies or probably more than 50 antibodies in the signature peptide targeting strategy for biomarker analysis where multiple peptides from each protein are being selected immunospecifically and quantified (Anderson et al., 2006, *Mol. Cell. Proteomics* 5: 573-588).

Another advantage of glycan-targeting is that antigens closely connected to the disease mechanism are being selected, as was the case with the Le$^x$ antigen herein. At least one third of the proteins selected by the anti-Le$^x$ antibody were elevated in cancer patients and these proteins are therefore potential cancer marker candidates. This is an unusually high hit rate. Still other advantages of the approach are the simplicity and degree of purification achieved in a single step. Depending on the sample, IAC provided a 1000-2000 fold reduction in sample mass and complexity. Finally there is the robustness of the method. A single IAC column was used to carry out the whole study without apparent loss of loading capacity. It is possible that other glycan-targeting antibodies should be equally efficacious in glycoprotein purification and identification.

The chromatographic separation in FIG. 8 shows that the degree of simplification obtained with IAC in the case of Le$^x$ antigen bearing proteins is sufficient to allow quantitative comparisons of cancer and control plasma by RPC, without mass spectrometry. As understanding of glycoprotein markers evolves, it may be possible to screen antibody selected glycoprotein marker candidates through chromatographic methods alone. Protein detection sensitivity with the 4.6 mm diameter RPC column used in herein was roughly equivalent to that of the mass spectrometer. Going to capillary columns would increase sensitivity another 1000-fold, requiring 30 µL or less of plasma for an analysis. A glycan-targeting antibody approach coupled with liquid chromatography could have the sensitivity, simplicity, and speed to be of utility in the clinical environment.

Based on the results from these Le$^x$ antigen experiments, it is concluded that the utility of glycan-targeting antibodies is at least equivalent to lectins in glycoproteomics applications involving very complex samples. Additionally, the high degree of selectivity and binding affinity of these antibodies along with the fact that disease associated glycans are being selected and enriched suggests this approach could be valuable in clinical diagnostics. Targeted affinity selection based on either natural or synthetic selectors could enable application of much simpler analytical devices in translational and clinical medicine that will easily reach the μg/mL detection range with little sample preparation.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of biochemistry, protein chemistry, and medical prevention and therapy, are within the scope of this invention. All publications, patents, and patent applications cited herein are incorporated by reference in their entirety for all purposes.

What is claimed is:

1. A method for detecting the presence, absence, progression, regression, or extent of a disease or disorder in a subject, comprising:
   a) obtaining two or more sample glycopeptides or glycoproteins from the subject;
   b) obtaining two or more reference glycopeptides or glycoproteins;
   c) comparing the sample glycopeptides or glycoproteins with the reference glycopeptides or glycoproteins using mass spectrometry; and
   d) detecting a difference in a glycosylation state between the sample glycopeptides or glycoproteins and the reference glycopeptides or glycoproteins;
      wherein a difference in the glycosylation state between the sample glycopeptides or glycoproteins and the reference glycopeptides or glycoproteins is indicative of the presence, absence, progression, regression, or extent of the disease or disorder.

2. The method of claim 1 where comparing the sample glycopeptides or glycoproteins with the reference glycopeptides or glycoproteins comprises using isotopically labeled internal standard peptides.

3. The method of claim 1 where comparing the sample glycopeptides or glycoproteins with the reference glycopeptides or glycoproteins comprises using global isotopic coding of glycopeptides or glycoproteins.

4. The method of claim 1 where comparing the sample glycopeptides or glycoproteins with the reference glycopeptides or glycoproteins comprises using liquid chromatography and absorbance or fluorescence.

5. The method of claim 1 where comparing the sample glycopeptides or glycoproteins with the reference glycopeptides or glycoproteins comprises immunological assaying of biomarkers from test subjects and disease-free subjects.

6. The method of claim 1 where the glycosylation state is due to at least one of fucosylation, sialylation, glucosylation, galactosylation, N-acetyl galactosylation, N-acetyl glucosylation, or mannosylation.

7. The method of claim 1 further comprising affinity selecting the glycopeptides or glycoproteins using lectin.

8. The method of claim 1 further comprising affinity selecting the glycopeptides or glycoproteins using antibodies.

9. The method of claim 1 where the disease is cancer.

10. A method for detecting the presence, absence, progression, regression, or extent of a disease or disorder in a subject, comprising:
    a) obtaining two or more sample glycopeptides or glycoproteins from the subject;
    b) obtaining two or more reference glycopeptides or glycoproteins;
    c) comparing the sample glycopeptides or glycoproteins with the reference glycopeptides or glycoproteins using mass spectrometry; and
    d) detecting a difference in concentration between the sample glycopeptides or glycoproteins and the reference glycopeptides or glycoproteins;
       wherein a difference in concentration between the sample glycopeptides or glycoproteins and the reference glycopeptides or glycoproteins is indicative of the presence, absence, progression, regression, or extent of the disease or disorder.

11. The method of claim 10 where the difference in concentration of glycopeptides or glycoproteins is due to a change in glycopeptide or glycoprotein mass.

12. The method of claim 10 where the change in concentration of glycopeptides or glycoproteins is due to a change in the amount of fucose, sialic acid, glucose, galactose, mannose, N-acetylgalactosamine, N-acetylglucosamine, Lewis antigen, or N-linked 13(1,6)-branching in the glycan portion of the glycoconjugate.

13. The method of claim 10 where the change in concentration of glycopeptides or glycoproteins is due to fucosylation.

14. The method of claim 10 where the change in the concentration of glycopeptides or glycoproteins is due to an antigenic glycan.

15. The method of claim 10 where the change in concentration of glycopeptides or glycoproteins is due to a Lewis antigen.

16. The method of diagnosing a disease which comprises the steps of:
    a) providing a sample which comprises at least two glycopeptides or glycoproteins;
    b) providing a reference which comprises at least two glycopeptides or glycoproteins; and
    c) comparing the concentration of the sample glycopeptides or glycoproteins with the concentration of the reference glycopeptides or glycoproteins using mass spectrometry;
       wherein a difference in the concentration between the sample glycopeptides or glycoproteins and the reference glycopeptides or glycoproteins is an indicator of the disease.

17. The method of claim 16 where the difference in the concentration of glycopeptides or glycoproteins comprises determining changes in glycopeptide or glycoprotein mass.

18. The method of claim 16 further comprising affinity selecting the glycopeptides or glycoproteins using a lectin or an antibody.

19. The method of claim 16 where comparing the concentration of the sample glycopeptides or glycoproteins with the concentration of the reference glycopeptides or glycoproteins comprises detecting changes in the concentration of at least one glycopeptide or glycoprotein.

20. The method of claim 16 where comparing the concentration of the sample glycopeptides or glycoproteins with the concentration of the reference glycopeptides or glycoproteins comprises detecting a change in the amount of fucose, sialic acid, glucose, galactose, mannose, N-acetylgalactosamine, Nacetylglucosamine, Lewis antigen, or N-linked 13(1,6)-branching in the glycan portion of the glycopeptides or glycoproteins.

21. The method of claim 16 where comparing the concentration of the sample glycopeptides or glycoproteins with the concentration of the reference glycopeptides or glycoproteins comprises detecting changes in fucosylation of the glycopeptides or glycoproteins.

22. The method of claim 16 where the disease is cancer.

23. A method of diagnosing a disease which comprises the steps of:
    a) providing a sample which comprises at least two glycopeptides or glycoproteins;
    b) providing a reference which comprises at least two glycopeptides or glycoproteins; and
    c) comparing the mass of the sample glycopeptides or glycoproteins with the mass of the reference glycopeptides or glycoproteins using mass spectrometry;
       wherein a difference in the mass between the sample glycopeptides or glycoproteins and the reference glycopeptides or glycoproteins is an indicator of the disease.

24. The method of claim 10 wherein the difference in concentration of glycopeptides or glycoproteins is due to a change in concentration of the peptide or protein portions of the glycopeptides or glycoproteins.

25. The method of claim 10 wherein the glycans are removed from the glycopeptides or glycoproteins before comparing them using mass spectroscopy.

* * * * *

SEQUENCE LISTING

```
<160> NUMBER OF SEQ ID NOS: 9

<210> SEQ ID NO 1
<211> LENGTH: 449
<212> TYPE: PRT
<213> ORGANISM: Homo sapiens

<400> SEQUENCE: 1

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
                20                  25                  30

Glu Met Ser Asn Gln Gly Ser Lys Tyr Val Asn Lys Glu Ile Gln Asn
            35                  40                  45

Ala Val Asn Gly Val Lys Gln Ile Lys Thr Leu Ile Glu Lys Thr Asn
        50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Pro Lys Ser Arg
        210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285
```

```
Arg His Asn Ser Thr Gly Cys Leu Arg Met Lys Asp Gln Cys Asp Lys
            290                 295                 300
Cys Arg Glu Ile Leu Ser Val Asp Cys Ser Thr Asn Asn Pro Ser Gln
305                 310                 315                 320
Ala Lys Leu Arg Arg Glu Leu Asp Glu Ser Leu Gln Val Ala Glu Arg
                    325                 330                 335
Leu Thr Arg Lys Tyr Asn Glu Leu Leu Lys Ser Tyr Gln Trp Lys Met
            340                 345                 350
Leu Asn Thr Ser Ser Leu Leu Glu Gln Leu Asn Glu Gln Phe Asn Trp
                355                 360                 365
Val Ser Arg Leu Ala Asn Leu Thr Gln Gly Glu Asp Gln Tyr Tyr Leu
    370                 375                 380
Arg Val Thr Thr Val Ala Ser His Thr Ser Asp Ser Asp Val Pro Ser
385                 390                 395                 400
Gly Val Thr Glu Val Val Lys Leu Phe Asp Ser Asp Pro Ile Thr
                    405                 410                 415
Val Thr Val Pro Val Glu Val Ser Arg Lys Asn Pro Lys Phe Met Glu
                420                 425                 430
Thr Val Ala Glu Lys Ala Leu Gln Glu Tyr Arg Lys Lys His Arg Glu
            435                 440                 445
Glu

<210> SEQ ID NO 2
<211> LENGTH: 866
<212> TYPE: PRT
<213> ORGANISM: Homo sapiens

<400> SEQUENCE: 2

Met Phe Ser Met Arg Ile Val Cys Leu Val Leu Ser Val Val Gly Thr
1               5                   10                  15
Ala Trp Thr Ala Asp Ser Gly Glu Gly Asp Phe Leu Ala Glu Gly Gly
            20                  25                  30
Gly Val Arg Gly Pro Arg Val Val Glu Arg His Gln Ser Ala Cys Lys
        35                  40                  45
Asp Ser Asp Trp Pro Phe Cys Ser Asp Glu Asp Trp Asn Tyr Lys Cys
    50                  55                  60
Pro Ser Gly Cys Arg Met Lys Gly Leu Ile Asp Glu Val Asn Gln Asp
65                  70                  75                  80
Phe Thr Asn Arg Ile Asn Lys Leu Lys Asn Ser Leu Phe Glu Tyr Gln
                85                  90                  95
Lys Asn Asn Lys Asp Ser His Ser Leu Thr Thr Asn Ile Met Glu Ile
            100                 105                 110
Leu Arg Gly Asp Phe Ser Ser Ala Asn Asn Arg Asp Asn Thr Tyr Asn
        115                 120                 125
Arg Val Ser Glu Asp Leu Arg Ser Arg Ile Glu Val Leu Lys Arg Lys
    130                 135                 140
Val Ile Glu Lys Val Gln His Ile Gln Leu Leu Gln Lys Asn Val Arg
145                 150                 155                 160
Ala Gln Leu Val Asp Met Lys Arg Leu Glu Val Asp Ile Asp Ile Lys
                165                 170                 175
Ile Arg Ser Cys Arg Gly Ser Cys Ser Arg Ala Leu Ala Arg Glu Val
            180                 185                 190
Asp Leu Lys Asp Tyr Glu Asp Gln Gln Lys Gln Leu Glu Gln Val Ile
        195                 200                 205
Ala Lys Asp Leu Leu Pro Ser Arg Asp Arg Gln His Leu Pro Leu Ile
```

-continued

```
                210                 215                 220
Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
                260                 265                 270

Gly Ser Thr Ser Tyr Gly Thr Gly Ser Glu Thr Glu Ser Pro Arg Asn
                275                 280                 285

Pro Ser Ser Ala Gly Ser Trp Asn Ser Gly Ser Ser Gly Pro Gly Ser
290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
                340                 345                 350

Arg Pro Gly Ser Thr Gly Thr Trp Asn Pro Gly Ser Ser Glu Arg Gly
                355                 360                 365

Ser Ala Gly His Trp Thr Ser Glu Ser Ser Val Ser Gly Ser Thr Gly
370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
                420                 425                 430

Leu Val Thr Ser Lys Gly Asp Lys Glu Leu Arg Thr Gly Lys Glu Lys
                435                 440                 445

Val Thr Ser Gly Ser Thr Thr Thr Arg Arg Ser Cys Ser Lys Thr
                450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
                500                 505                 510

His Pro Asp Glu Ala Ala Phe Phe Asp Thr Ala Ser Thr Gly Lys Thr
                515                 520                 525

Phe Pro Gly Phe Phe Ser Pro Met Leu Gly Glu Phe Val Ser Glu Thr
                530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
                580                 585                 590

Asp Ser Thr Phe Glu Ser Lys Ser Tyr Lys Met Ala Asp Glu Ala Gly
                595                 600                 605

Ser Glu Ala Asp His Glu Gly Thr His Ser Thr Lys Arg Gly His Ala
                610                 615                 620

Lys Ser Arg Pro Val Arg Asp Cys Asp Asp Val Leu Gln Thr His Pro
625                 630                 635                 640
```

```
Ser Gly Thr Gln Ser Gly Ile Phe Asn Ile Lys Leu Pro Gly Ser Ser
            645                 650                 655

Lys Ile Phe Ser Val Tyr Cys Asp Gln Glu Thr Ser Leu Gly Gly Trp
            660                 665                 670

Leu Leu Ile Gln Gln Arg Met Asp Gly Ser Leu Asn Phe Asn Arg Thr
            675                 680                 685

Trp Gln Asp Tyr Lys Arg Gly Phe Gly Ser Leu Asn Asp Glu Gly Glu
            690                 695                 700

Gly Glu Phe Trp Leu Gly Asn Asp Tyr Leu His Leu Leu Thr Gln Arg
705                 710                 715                 720

Gly Ser Val Leu Arg Val Glu Leu Glu Asp Trp Ala Gly Asn Glu Ala
            725                 730                 735

Tyr Ala Glu Tyr His Phe Arg Val Gly Ser Glu Ala Glu Gly Tyr Ala
            740                 745                 750

Leu Gln Val Ser Ser Tyr Glu Gly Thr Ala Gly Asp Ala Leu Ile Glu
            755                 760                 765

Gly Ser Val Glu Glu Gly Ala Glu Tyr Thr Ser His Asn Asn Met Gln
            770                 775                 780

Phe Ser Thr Phe Asp Arg Asp Ala Asp Gln Trp Glu Glu Asn Cys Ala
785                 790                 795                 800

Glu Val Tyr Gly Gly Gly Trp Trp Tyr Asn Asn Cys Gln Ala Ala Asn
            805                 810                 815

Leu Asn Gly Ile Tyr Tyr Pro Gly Gly Ser Tyr Asp Pro Arg Asn Asn
            820                 825                 830

Ser Pro Tyr Glu Ile Glu Asn Gly Val Val Trp Val Ser Phe Arg Gly
            835                 840                 845

Ala Asp Tyr Ser Leu Arg Ala Val Arg Met Lys Ile Arg Pro Leu Val
850                 855                 860

Thr Gln
865

<210> SEQ ID NO 3
<211> LENGTH: 491
<212> TYPE: PRT
<213> ORGANISM: Homo sapiens

<400> SEQUENCE: 3

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
            35                  40                  45

Leu Asp Lys Lys Arg Glu Glu Ala Pro Ser Leu Arg Pro Ala Pro Pro
        50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
            85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
            115                 120                 125

Glu Leu Asn Asn Asn Val Glu Ala Val Ser Gln Thr Ser Ser Ser Ser
        130                 135                 140
```

```
Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
            165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
        195                 200                 205

Ile Gln Lys Leu Glu Ser Asp Val Ser Ala Gln Met Glu Tyr Cys Arg
210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255

Ile Gln Pro Asp Ser Ser Val Lys Pro Tyr Arg Val Tyr Cys Asp Met
            260                 265                 270

Asn Thr Glu Asn Gly Gly Trp Thr Val Ile Gln Asn Arg Gln Asp Gly
        275                 280                 285

Ser Val Asp Phe Gly Arg Lys Trp Asp Pro Tyr Lys Gln Gly Phe Gly
290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335

Pro Thr Glu Leu Leu Ile Glu Met Glu Asp Trp Lys Gly Asp Lys Val
            340                 345                 350

Lys Ala His Tyr Gly Gly Phe Thr Val Gln Asn Glu Ala Asn Lys Tyr
        355                 360                 365

Gln Ile Ser Val Asn Lys Tyr Arg Gly Thr Ala Gly Asn Ala Leu Met
370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
                405                 410                 415

Thr Ser Asp Pro Arg Lys Gln Cys Ser Lys Glu Asp Gly Gly Gly Trp
            420                 425                 430

Trp Tyr Asn Arg Cys His Ala Ala Asn Pro Asn Gly Arg Tyr Tyr Trp
        435                 440                 445

Gly Gly Gln Tyr Thr Trp Asp Met Ala Lys His Gly Thr Asp Asp Gly
450                 455                 460

Val Val Trp Met Asn Trp Lys Gly Ser Trp Tyr Ser Met Arg Lys Met
465                 470                 475                 480

Ser Met Lys Ile Arg Pro Phe Phe Pro Gln Gln
                485                 490

<210> SEQ ID NO 4
<211> LENGTH: 454
<212> TYPE: PRT
<213> ORGANISM: Homo sapiens

<400> SEQUENCE: 4

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30
```

```
Phe Leu Pro Asp Ser Ile Thr Phe Ser Trp Lys Tyr Lys Asn Asn Ser
             35                  40                  45

Asp Ile Ser Ser Thr Arg Gly Phe Pro Ser Val Leu Arg Gly Gly Lys
 50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                 85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Gly Asn Pro Arg
                115                 120                 125

Ser Lys Ser Lys Leu Ile Cys Gln Ala Thr Gly Phe Ser Pro Arg Gln
            130                 135                 140

Ile Gln Val Ser Trp Leu Arg Glu Gly Lys Gln Val Gly Ser Gly Val
145                 150                 155                 160

Thr Thr Asp Gln Val Gln Ala Glu Ala Lys Glu Ser Gly Pro Thr Thr
                165                 170                 175

Tyr Lys Val Thr Ser Thr Leu Thr Ile Lys Glu Ser Asp Trp Leu Ser
            180                 185                 190

Gln Ser Met Phe Thr Cys Arg Val Asp His Arg Gly Leu Thr Phe Gln
            195                 200                 205

Gln Asn Ala Ser Ser Met Cys Val Pro Asp Gln Asp Thr Ala Ile Arg
210                 215                 220

Val Phe Ala Ile Pro Pro Ser Phe Ala Ser Ile Phe Leu Thr Lys Ser
225                 230                 235                 240

Thr Lys Leu Thr Cys Leu Val Thr Asp Leu Thr Thr Tyr Asp Ser Val
                245                 250                 255

Thr Ile Ser Trp Thr Arg Gln Asn Gly Glu Ala Val Lys Thr His Thr
            260                 265                 270

Asn Ile Ser Glu Ser His Pro Asn Ala Thr Phe Ser Ala Val Gly Glu
            275                 280                 285

Ala Ser Ile Cys Glu Asp Asp Trp Asn Ser Gly Glu Arg Phe Thr Cys
290                 295                 300

Thr Val Thr His Thr Asp Leu Pro Ser Pro Leu Lys Gln Thr Ile Ser
305                 310                 315                 320

Arg Pro Lys Gly Val Ala Leu His Arg Pro Asp Val Tyr Leu Leu Pro
                325                 330                 335

Pro Ala Arg Glu Gln Leu Asn Leu Arg Glu Ser Ala Thr Ile Thr Cys
                340                 345                 350

Leu Val Thr Gly Phe Ser Pro Ala Asp Val Phe Val Gln Trp Met Gln
                355                 360                 365

Arg Gly Gln Pro Leu Ser Pro Glu Lys Tyr Val Thr Ser Ala Pro Met
370                 375                 380

Pro Glu Pro Gln Ala Pro Gly Arg Tyr Phe Ala His Ser Ile Leu Thr
385                 390                 395                 400

Val Ser Glu Glu Trp Asn Thr Gly Glu Thr Tyr Thr Cys Val Val
                405                 410                 415

Ala His Glu Ala Leu Pro Asn Arg Val Thr Glu Arg Thr Val Asp Lys
                420                 425                 430

Ser Thr Gly Lys Pro Thr Leu Tyr Asn Val Ser Leu Val Met Ser Asp
            435                 440                 445

Thr Ala Gly Thr Cys Tyr
            450
```

<210> SEQ ID NO 5
<211> LENGTH: 644
<212> TYPE: PRT
<213> ORGANISM: Homo sapiens

<400> SEQUENCE: 5

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
    50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
        115                 120                 125

Thr Pro Ala Glu Gly Pro Val Val Thr Ala Gln Tyr Asp Cys Leu Gly
    130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Asn Thr Gln His Ser Ser Leu
                165                 170                 175

Phe Met Leu Asn Glu Val Lys Arg Ala Gln Arg Gln Val Val Ala Gly
            180                 185                 190

Leu Asn Phe Arg Ile Thr Tyr Ser Ile Val Gln Thr Asn Cys Ser Lys
        195                 200                 205

Glu Asn Phe Leu Phe Leu Thr Pro Asp Cys Lys Ser Leu Trp Asn Gly
    210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
            260                 265                 270

Thr Asn Ser Pro Glu Leu Glu Glu Thr Leu Thr His Thr Ile Thr Lys
        275                 280                 285

Leu Asn Ala Glu Asn Asn Ala Thr Phe Tyr Phe Lys Ile Asp Asn Val
    290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
            340                 345                 350

Ala Glu Val Tyr Val Val Pro Trp Glu Lys Lys Ile Tyr Pro Thr Val
        355                 360                 365

Asn Cys Gln Pro Leu Gly Met Ile Ser Leu Met Lys Arg Pro Pro Gly
    370                 375                 380

Phe Ser Pro Phe Arg Ser Arg Ile Gly Glu Ile Lys Glu Thr
385                 390                 395                 400

Thr Val Ser Pro Pro His Thr Ser Met Ala Pro Ala Gln Asp Glu Glu
            405                 410                 415

Arg Asp Ser Gly Lys Glu Gln Gly His Thr Arg Arg His Asp Trp Gly
        420                 425                 430

His Glu Lys Gln Arg Lys His Asn Leu Gly His Gly His Lys His Glu
    435                 440                 445

Arg Asp Gln Gly His Gly His Gln Arg Gly His Gly Leu Gly His Gly
450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
                485                 490                 495

His Lys His Gly His Gly His Gly Lys His Lys Asn Lys Gly Lys Lys
            500                 505                 510

Asn Gly Lys His Asn Gly Trp Lys Thr Glu His Leu Ala Ser Ser Ser
        515                 520                 525

Glu Asp Ser Thr Thr Pro Ser Ala Gln Thr Gln Leu Lys Thr Glu Gly
530                 535                 540

Pro Thr Pro Ile Pro Ser Leu Ala Lys Pro Gly Val Thr Val Thr Phe
545                 550                 555                 560

Ser Asp Phe Gln Asp Ser Asp Leu Ile Ala Thr Met Met Pro Pro Ile
                565                 570                 575

Ser Pro Ala Pro Ile Gln Ser Asp Asp Asp Trp Ile Pro Asp Ile Gln
            580                 585                 590

Ile Asp Pro Asn Gly Leu Ser Phe Asn Pro Ile Ser Asp Phe Pro Asp
        595                 600                 605

Thr Thr Ser Pro Lys Cys Pro Gly Arg Pro Trp Lys Ser Val Ser Glu
610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 6
<211> LENGTH: 101
<212> TYPE: PRT
<213> ORGANISM: Homo sapiens

<400> SEQUENCE: 6

Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
            20                  25                  30

Ala Glu Glu Asp Gly Asp Leu Gln Cys Leu Cys Val Lys Thr Thr Ser
        35                  40                  45

Gln Val Arg Pro Arg His Ile Thr Ser Leu Glu Val Ile Lys Ala Gly
    50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95

Lys Leu Leu Glu Ser
            100

```
<210> SEQ ID NO 7
<211> LENGTH: 104
<212> TYPE: PRT
<213> ORGANISM: Homo sapiens

<400> SEQUENCE: 7

Met Ser Ser Ala Ala Arg Ser Arg Leu Thr Arg Ala Thr Arg Gln Glu
1               5                   10                  15

Met Leu Phe Leu Ala Leu Leu Leu Pro Val Val Ala Phe Ala
            20                  25                  30

Arg Ala Glu Ala Glu Glu Asp Gly Asp Leu Gln Cys Leu Cys Val Lys
            35                  40                  45

Thr Thr Ser Gln Val Arg Pro Arg His Ile Thr Ser Leu Glu Val Ile
50                  55                  60

Lys Ala Gly Pro His Cys Pro Thr Ala Gln Leu Ile Ala Thr Leu Lys
65                  70                  75                  80

Asn Gly Arg Lys Ile Cys Leu Asp Leu Gln Ala Leu Leu Tyr Lys Lys
                85                  90                  95

Ile Ile Lys Glu His Leu Glu Ser
            100

<210> SEQ ID NO 8
<211> LENGTH: 122
<212> TYPE: PRT
<213> ORGANISM: Homo sapiens

<400> SEQUENCE: 8

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
            35                  40                  45

Gly Ser Asp Lys Tyr Phe His Ala Arg Gly Asn Tyr Asp Ala Ala Lys
50                  55                  60

Arg Gly Pro Gly Gly Val Trp Ala Ala Glu Ala Ile Ser Asp Ala Arg
65                  70                  75                  80

Glu Asn Ile Gln Arg Phe Phe Gly His Gly Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
            115                 120

<210> SEQ ID NO 9
<211> LENGTH: 477
<212> TYPE: PRT
<213> ORGANISM: Homo sapiens

<400> SEQUENCE: 9

Met Ala Pro Leu Arg Pro Leu Leu Ile Leu Ala Leu Leu Ala Trp Val
1               5                   10                  15

Ala Leu Ala Asp Gln Glu Ser Cys Lys Gly Arg Cys Thr Glu Gly Phe
            20                  25                  30

Asn Val Asp Lys Lys Cys Gln Cys Asp Glu Leu Cys Ser Tyr Tyr Gln
            35                  40                  45

Ser Cys Cys Thr Asp Tyr Thr Ala Glu Cys Lys Pro Gln Val Thr Arg
50                  55                  60
```

-continued

```
Gly Asp Val Phe Thr Met Pro Glu Asp Glu Tyr Thr Val Tyr Asp Asp
 65                  70                  75                  80

Gly Glu Glu Lys Asn Asn Ala Thr Val His Glu Gln Val Gly Gly Pro
                 85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Ala Pro Ala Pro Glu Val Gly
            115                 120                 125

Ala Ser Lys Pro Glu Gly Ile Asp Ser Arg Pro Glu Thr Leu His Pro
130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
                165                 170                 175

Gly Gln Tyr Cys Tyr Glu Leu Asp Glu Lys Ala Val Arg Pro Gly Tyr
                180                 185                 190

Pro Lys Leu Ile Arg Asp Val Trp Gly Ile Glu Gly Pro Ile Asp Ala
            195                 200                 205

Ala Phe Thr Arg Ile Asn Cys Gln Gly Lys Thr Tyr Leu Phe Lys Gly
            210                 215                 220

Ser Gln Tyr Trp Arg Phe Glu Asp Gly Val Leu Asp Pro Asp Tyr Pro
225                 230                 235                 240

Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
            275                 280                 285

Ser Gln Glu Glu Cys Glu Gly Ser Ser Leu Ser Ala Val Phe Glu His
            290                 295                 300

Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
                340                 345                 350

Arg Ile Tyr Ile Ser Gly Met Ala Pro Arg Pro Ser Leu Ala Lys Lys
            355                 360                 365

Gln Arg Phe Arg His Arg Asn Arg Lys Gly Tyr Arg Ser Gln Arg Gly
370                 375                 380

His Ser Arg Gly Arg Asn Gln Asn Ser Arg Pro Ser Arg Ala Thr
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
            420                 425                 430

Ile Gln Ser Val Phe Phe Phe Ser Gly Asp Lys Tyr Tyr Arg Val Asn
            435                 440                 445

Leu Arg Thr Arg Arg Val Asp Thr Val Asp Pro Pro Tyr Pro Arg Ser
            450                 455                 460

Ile Ala Gln Tyr Trp Leu Gly Cys Pro Ala Pro Gly His
465                 470                 475
```